United States Patent
Cohen et al.

(10) Patent No.: US 11,285,052 B2
(45) Date of Patent: Mar. 29, 2022

(54) TAMPON

(71) Applicant: Kimberly-Clark Worldwide, Inc., Neenah, WI (US)

(72) Inventors: Bliss Elizabeth Cohen, Appleton, WI (US); Steven Craig Gehling, Oshkosh, WI (US); David Kevin Oldroyd, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 443 days.

(21) Appl. No.: 16/319,847

(22) PCT Filed: Jul. 27, 2017

(86) PCT No.: PCT/US2017/044092
§ 371 (c)(1),
(2) Date: Jan. 23, 2019

(87) PCT Pub. No.: WO2018/022836
PCT Pub. Date: Feb. 1, 2018

(65) Prior Publication Data
US 2019/0269561 A1 Sep. 5, 2019

Related U.S. Application Data

(60) Provisional application No. 62/368,504, filed on Jul. 29, 2016.

(51) Int. Cl.
*A61F 13/20* (2006.01)
*A61F 13/34* (2006.01)

(52) U.S. Cl.
CPC .......... *A61F 13/2037* (2013.01); *A61F 13/20* (2013.01); *A61F 13/202* (2013.01);
(Continued)

(58) Field of Classification Search
CPC .... A61F 13/20; A61F 13/202; A61F 13/2034; A61F 13/2037; A61F 13/2031; A61F 13/34; A61F 13/2054
(Continued)

(56) References Cited

U.S. PATENT DOCUMENTS 2,798,260 A 7/1957 Niepmann et al.
3,422,496 A 1/1969 Wolff et al.
(Continued)

FOREIGN PATENT DOCUMENTS

CA 2365459 A1 8/2001
CA 2442271 9/2003
(Continued)

OTHER PUBLICATIONS

US 8,910,354 B2, 12/2014, Amundson et al. (withdrawn)
Co-Pending U.S. Appl. No. 16/319,850, filed Jan. 23, 2019, by Gehling et al. for "Method of Manufacturing a Tampon."

*Primary Examiner* — Jacqueline F Stephens
(74) *Attorney, Agent, or Firm* — Kimberly-Clark Worldwide, Inc.

(57) ABSTRACT

In the manufacture of a tampon, an absorbent structure composed of an absorbent material can be formed into a tampon blank. In various embodiments, a withdrawal element can be attached to the absorbent structure either before or after the absorbent structure is formed into a tampon blank. The tampon blank can then undergo a compression step which can result in the pledget of the tampon. The pledget, and resultant tampon, can have at least one linear channel and at least one non-linear channel.

11 Claims, 25 Drawing Sheets

(52) U.S. Cl.
CPC ...... *A61F 13/2034* (2013.01); *A61F 13/2054* (2013.01); *A61F 13/34* (2013.01)

(58) Field of Classification Search
USPC .................................. 604/385.17, 385.18
See application file for complete search history.

(56) References Cited

U.S. PATENT DOCUMENTS

| | | | |
|---|---|---|---|
| 5,592,725 | A | 1/1997 | Brinker |
| 6,177,608 | B1 | 1/2001 | Weinstrauch |
| 6,310,269 | B1 | 10/2001 | Friese et al. |
| 7,549,982 | B2 | 6/2009 | Carlin |
| 7,967,803 | B2 | 6/2011 | Van Ingelgem et al. |
| 7,994,387 | B2 | 8/2011 | Minoguchi et al. |
| 8,468,662 | B2 | 6/2013 | Rolli et al. |
| 8,474,114 | B2 | 7/2013 | Rolli |
| 8,747,378 | B2 | 6/2014 | Van Ingelgem et al. |
| 8,834,439 | B2 | 9/2014 | Kimball et al. |
| 8,938,866 | B2 | 1/2015 | Amundson et al. |
| 9,155,665 | B2 | 10/2015 | Magnusson et al. |
| 9,155,666 | B2 | 10/2015 | Smet et al. |
| 9,168,184 | B2 | 10/2015 | Kimball et al. |
| 10,010,457 | B2 | 7/2018 | Kimball et al. |
| 2002/0151859 | A1 | 10/2002 | Schoelling |
| 2004/0030280 | A1* | 2/2004 | Mercier ............. A61F 13/2051 604/11 |
| 2005/0113787 | A1 | 5/2005 | Carlin |
| 2005/0113807 | A1* | 5/2005 | Carlin ................ A61F 13/2031 604/358 |
| 2011/0092940 | A1 | 4/2011 | Fung et al. |
| 2011/0238028 | A1* | 9/2011 | Smet .................. A61F 13/2085 604/385.17 |
| 2012/0010587 | A1 | 1/2012 | Smet |
| 2012/0089111 | A1* | 4/2012 | Magnusson ......... A61F 13/2037 604/385.18 |
| 2012/0187600 | A1 | 7/2012 | Graber |
| 2012/0283685 | A1 | 11/2012 | Amundson et al. |
| 2013/0062812 | A9 | 3/2013 | Graber |
| 2013/0110074 | A1 | 5/2013 | Smet et al. |
| 2014/0088539 | A1 | 3/2014 | Kimball et al. |
| 2014/0088540 | A1 | 3/2014 | Kimball et al. |
| 2014/0088541 | A1 | 3/2014 | Kimball et al. |
| 2014/0090219 | A1 | 4/2014 | Gehling et al. |
| 2015/0164702 | A1* | 6/2015 | Mueller ............... A61F 13/206 604/369 |
| 2016/0022507 | A1 | 1/2016 | Kimball et al. |

FOREIGN PATENT DOCUMENTS

| | | |
|---|---|---|
| CA | 2827986 A1 | 3/2014 |
| CN | 1878524 A | 12/2006 |
| DE | 19825877 C1 | 11/1999 |
| DE | 10244874 A1 | 4/2004 |
| DE | 102005050514 A1 | 4/2007 |
| EP | 1383453 B1 | 8/2006 |
| EP | 1561443 B1 | 8/2008 |
| EP | 1983953 B1 | 1/2010 |
| EP | 2404584 A1 | 1/2012 |
| EP | 2590608 B1 | 11/2014 |
| KR | 1020120046206 A | 5/2012 |
| WO | 0018345 A1 | 4/2000 |
| WO | 2008095937 A2 | 8/2008 |
| WO | 2009129910 A1 | 10/2009 |
| WO | 2011000507 A1 | 1/2011 |
| WO | 2011002357 A1 | 1/2011 |

* cited by examiner

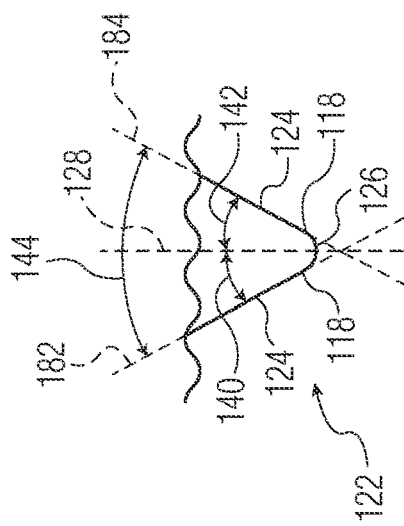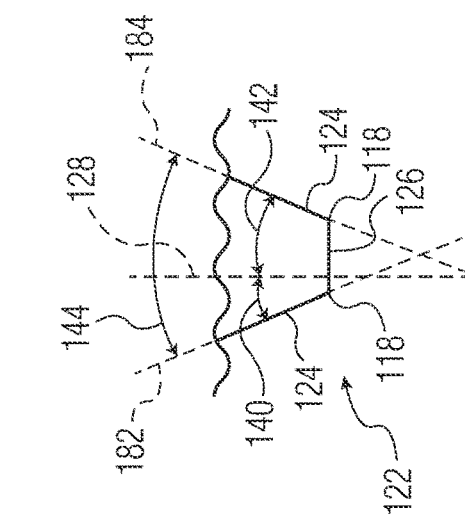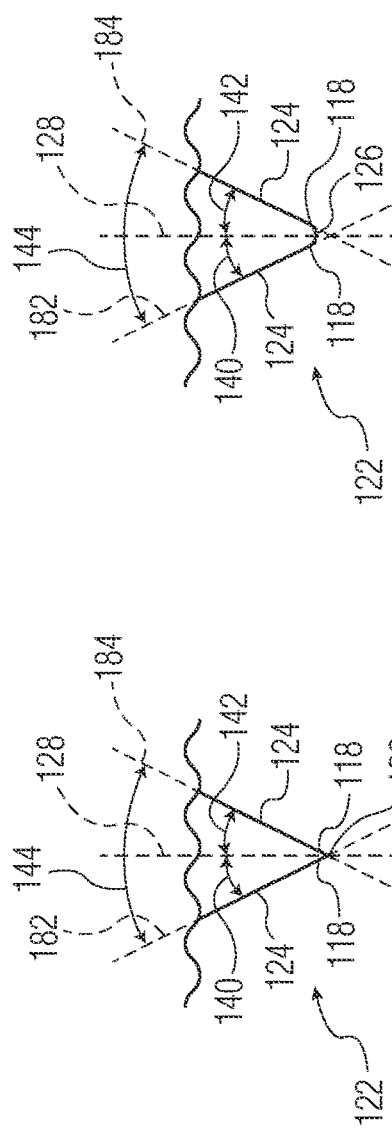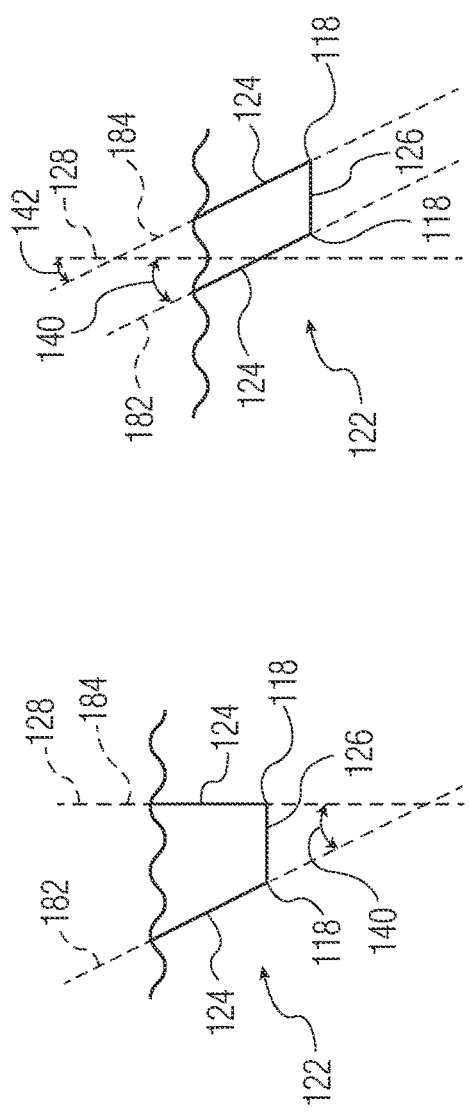

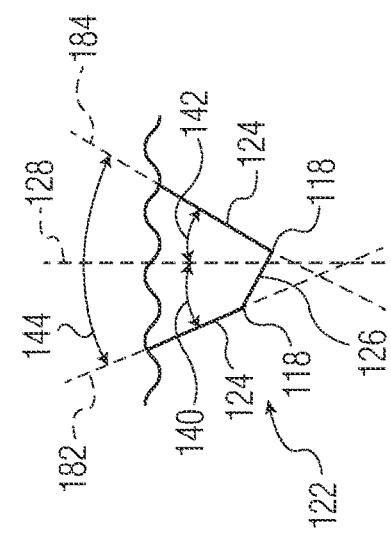
FIG. 8G
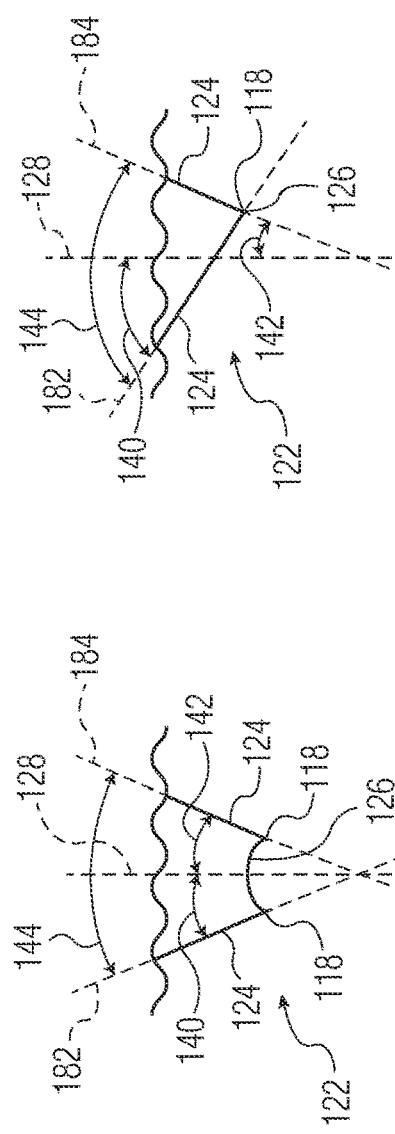
FIG. 8J
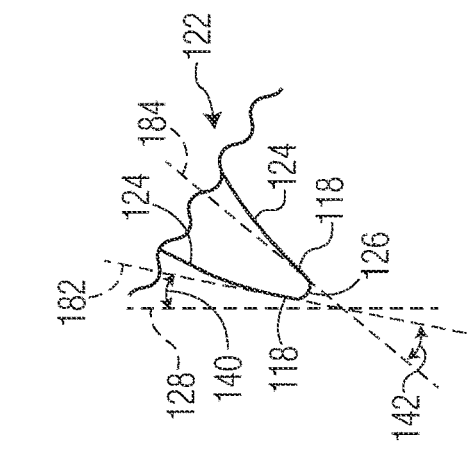
FIG. 8H
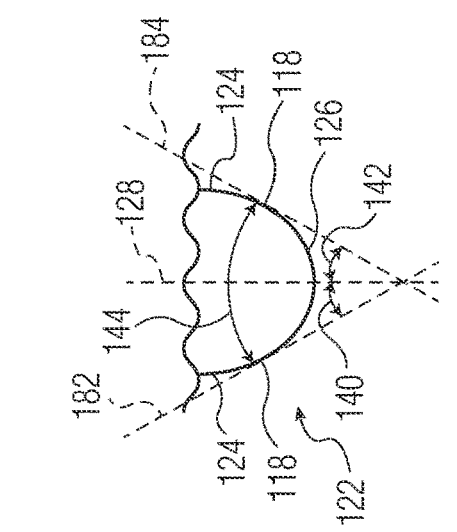
FIG. 8K
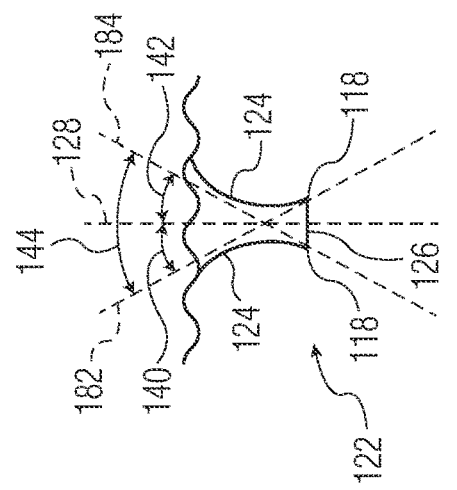
FIG. 8I
FIG. 8L

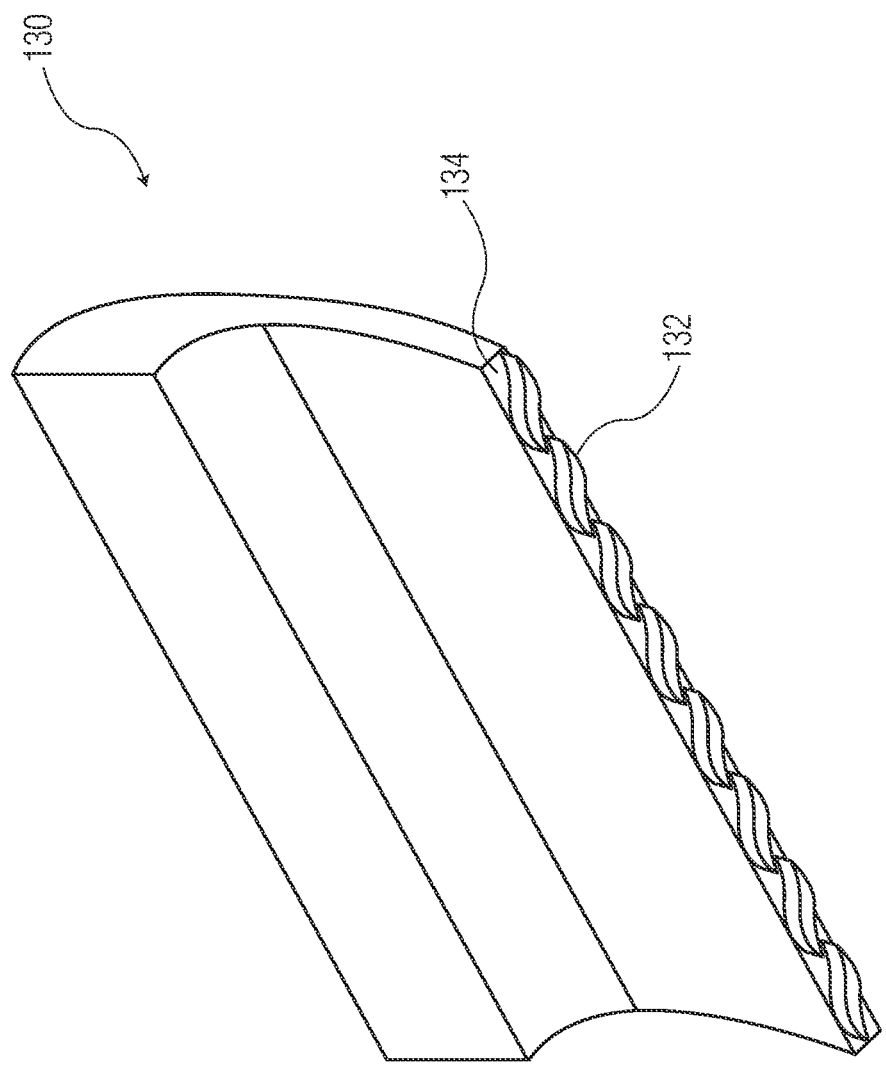

TAMPON

RELATED APPLICATION

The present application claims priority to U.S. Provisional Application No. 62/368,504, filed Jul. 29, 2016, the contents of which are hereby incorporated by reference in a manner consistent with the present application.

BACKGROUND OF THE DISCLOSURE

A wide variety of products can undergo a compression step during a manufacturing process of the product. Compression of the product can alter the dimensions of the product from its original starting dimensions and reduce those dimensions to render a product with final smaller dimensions. An example of a personal care product which can undergo a compression step in a manufacturing process is a tampon.

Tampons generally undergo a compression step during the manufacturing process in order to render a tampon having a size and dimension more suitable for insertion into the body of the user. The compression of a tampon blank can result in a tampon capable of being inserted digitally by the user's fingers or through the use of an applicator. A tampon is generally manufactured by folding, rolling, or stacking an absorbent structure made of loosely associated absorbent material into a tampon blank. The tampon blank can then be compressed into a tampon of the desired size and shape.

In use, tampons are designed to be inserted into a woman's vagina to intercept the fluid flow of menses, blood, and other body fluids and to prevent fluid from exiting the vagina. As body fluids contact the tampon they should be absorbed and retained by the absorbent material of the tampon. After a time period, the tampon and its retained fluid is removed and disposed.

A drawback often encountered with tampons is the tendency toward premature failure of the tampon. For example, in general, tampons are formed from a compression process that results in straight grooves within the tampon. Such straight grooves can provide a pathway for body fluids to propagate unimpeded from the insertion end to the withdrawal end of the tampon without being sufficiently absorbed by the tampon. The premature failure of the tampon can result in leakage of body fluid from the vagina while the tampon is in place and before the tampon is completely saturated with the body fluid.

There is a need to provide a tampon which can have an improved handling of body fluid. There is a need to provide a tampon in which at least a portion of the grooves are not straight such that any potential fluid path for body exudates is lengthened thereby providing increased retention time for the body fluid to be absorbed by the tampon. There is a need to provide a manufacturing process which can manufacture such a tampon.

SUMMARY OF THE DISCLOSURE

In various embodiments, a tampon can have a compressed absorbent pledget which can have a longitudinal axis, an insertion end, a withdrawal end, an outer surface, and a longitudinal length measured from the insertion end to the withdrawal end; a longitudinal direction, a circumferential direction, and a radial depth direction; a linear channel extending in the longitudinal direction of the pledget; a non-linear channel which undulates in the radial depth direction of the pledget and has at least one crest and at least two troughs in the radial depth direction of the pledget wherein a distance between each trough is less than about 8 mm, and wherein the non-linear channel has a first outer surface edge and a second outer surface edge opposed to the first outer surface edge and separated from the first outer surface edge a variable width in the circumferential direction of the pledget at the outer surface of the compressed absorbent pledget; and a withdrawal string extending from the withdrawal end of the compressed absorbent pledget.

In various embodiments, the non-linear channel further comprises an undulation in the circumferential direction. In various embodiments, the non-linear channel further comprises a first channel sidewall extending from the first outer surface edge and in a direction toward the longitudinal axis; a second channel sidewall extending from the second outer surface edge and in a direction toward the longitudinal axis wherein the first channel sidewall and the second channel sidewall join together at an inner surface; a first region wherein the inner surface is located at a first depth below the outer surface and a second region wherein the inner surface is located at a second depth below the outer surface wherein the second depth is closer to the longitudinal axis than the first depth. In various embodiments, a distance between the first depth and the outer surface is from about 0.25 mm to about 0.75 mm. In various embodiments, a distance between the second depth and the outer surface is from about 0.8 mm to about 1.35 mm.

In various embodiments, a tampon can have at least two non-linear channels wherein the undulations in the circumferential direction of the first of the at least two non-linear channels is congruent with the undulations in the circumferential direction of a second of the at least two non-linear channels.

In various embodiments, a tampon can have a compressed absorbent pledget which can have a longitudinal axis; an insertion end, a withdrawal end, an outer surface, and a longitudinal length measured from the insertion end to the withdrawal end; a longitudinal direction, a circumferential direction, and a radial depth direction; a linear channel extending in the longitudinal direction of the pledget; a non-linear channel which undulates in the circumferential direction and undulates in the radial depth direction; and a withdrawal string extending from the withdrawal end of the compressed absorbent pledget.

In various embodiments, the non-linear channel further comprises a first outer surface edge and a second outer surface edge opposed to the first outer surface edge and separated from the first outer surface edge in the circumferential direction at the outer surface of the compressed absorbent pledget; a first channel sidewall extending from the first outer surface edge and in a direction toward the longitudinal axis; a second channel sidewall extending from the second outer surface edge and in a direction toward the longitudinal axis; a first region wherein the first outer surface edge is separated from the second outer surface edge by a uniform width in the circumferential direction at the outer surface of the pledget and wherein the first channel sidewall and the second channel sidewall join together at an inner surface located at a first depth below the outer surface; and a second region wherein the first outer surface edge is separated from the second outer surface edge by a variable width in the circumferential direction at the outer surface and wherein the first channel sidewall and the second channel sidewall join together at an inner surface located at a second depth below the outer surface of the pledget wherein the second depth is closer to the longitudinal axis than the first depth.

In various embodiments, a distance between the first depth and the outer surface is from about 0.25 mm to about 0.75 mm. In various embodiments, a distance between the second depth and the outer surface is from about 0.8 mm to about 1.35 mm. In various embodiments, the non-linear channel comprises a plurality of first regions and a plurality of second regions wherein the first regions and the second regions are positioned in an alternating sequence in the longitudinal direction of the tampon.

In various embodiments, the tampon comprises at least two non-linear channels wherein the undulations in the circumferential direction of a first of the at least two non-linear channels is congruent with the undulations in the circumferential direction of a second of the at least two non-linear channels.

In various embodiments, the tampon further comprises a plurality of linear channels and a plurality of non-linear channels wherein the linear channels and the non-linear channels are positioned in an alternating sequence.

In various embodiments, the undulations in the depth direction of the non-linear channel have at least 2 radial depth direction troughs.

BRIEF DESCRIPTION OF DRAWINGS

FIGS. 8A-8L are lateral cross-sectional end view illustrations of exemplary embodiments of compression segments.

FIG. 9A is a perspective view of an exemplary embodiment of a penetration jaw.

Figure 1A:
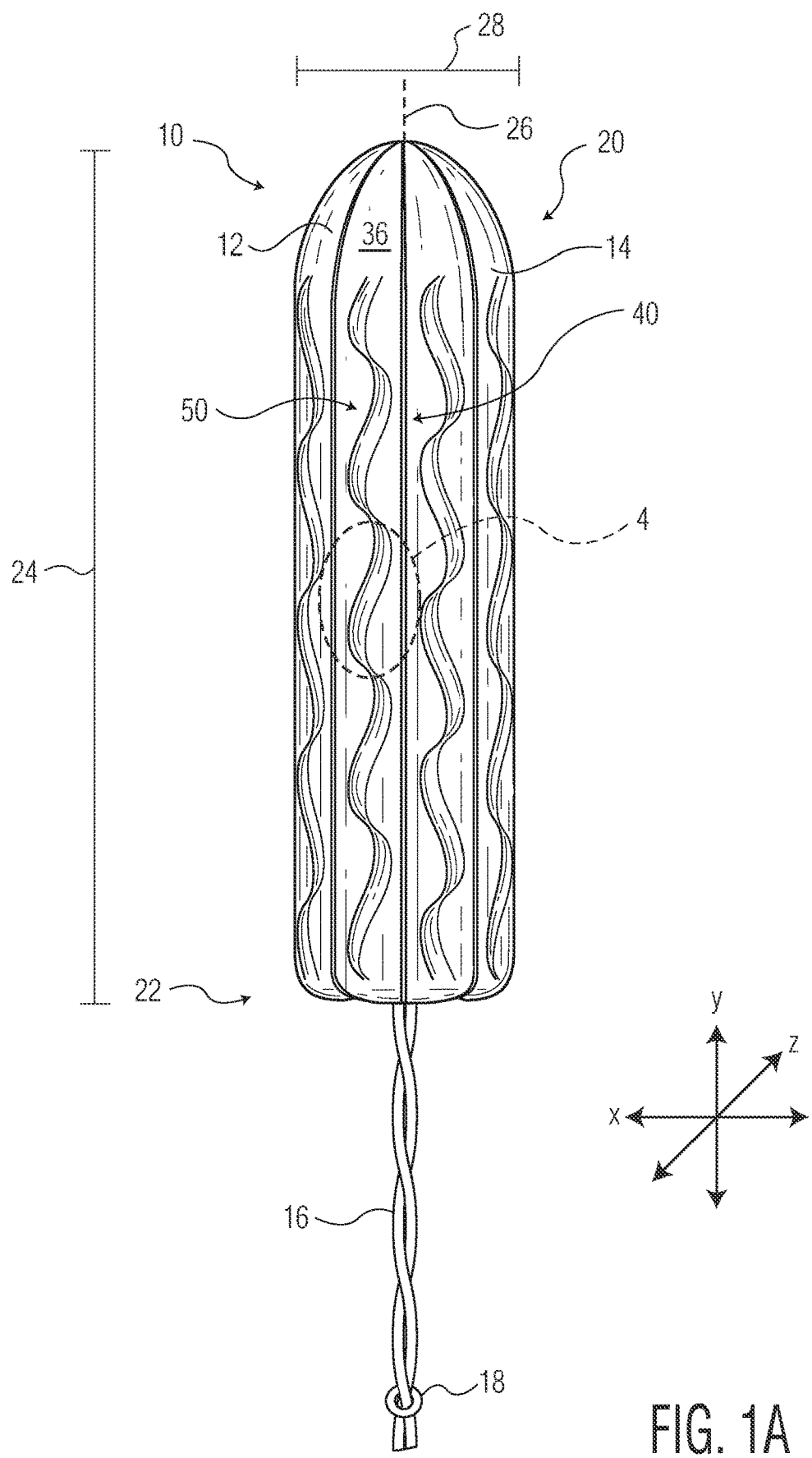
FIGS. 1A-1C are side views of exemplary embodiments of tampons.

Repeat use of reference characters in the present specification and drawings is intended to represent the same or analogous features or elements of the disclosure.

DETAILED DESCRIPTION OF THE DISCLOSURE

The present disclosure is directed towards a tampon designed to be inserted above the introital region of a woman's vaginal cavity. The tampon is designed to function so as to intercept body fluids such as menses, blood, and other body fluids and prevent the body fluids from exiting the vaginal cavity. In the manufacture of a tampon, an absorbent structure composed of an absorbent material can be formed into a tampon blank. In various embodiments, a withdrawal element can be attached to the absorbent structure either before or after the absorbent structure is formed into a tampon blank. The tampon blank can then undergo a compression step which can result in the pledget of the tampon. The pledget, and resultant tampon, can have at least one linear channel and at least one non-linear channel.

Definitions

The term "applicator" refers herein to a device that facilitates the insertion of a tampon into the vaginal cavity of a female. Non-limiting examples of such include any known hygienically designed applicator that is capable of receiving a tampon, including the so-called telescoping, barrel and plunger, and compact applicators.

The term "attached" refers herein to configurations in which a first element is secured to a second element by joining the first element to the second element. Joining the first element to the second element can occur by joining the first element directly to the second element, indirectly such as by joining the first element to an intermediate member(s) which in turn can be joined to the second element, and in configurations in which the first element is integral with the second element (i.e., the first element is essentially part of the second element). Attachment can occur by any method deemed suitable including, but not limited to, adhesives, ultrasonic bonds, thermal bonds, pressure bonds, mechanical entanglement, hydroentanglement, microwave bonds, sewing, or any other conventional technique. The attachment can extend continuously along the length of attachment, or it may be applied in an intermittent fashion at discrete intervals.

The term "bicomponent fiber" refers herein to fibers that have been formed from at least two different polymers extruded from separate extruders but spun together to form one fiber. Bicomponent fibers are also sometimes referred to as conjugate fibers or multicomponent fibers. The polymers can be arranged in substantially constantly positioned distinct zones across the cross-section of the bicomponent fiber and can extend continuously along the length of the bicomponent fiber. The configuration of such a bicomponent fiber may be, for example, a sheath/core arrangement wherein one polymer is surrounded by another or may be a side-by-side arrangement, a pie arrangement, or an "islands-in-the-sea" arrangement.

The term "blank" refers herein to a construction of an absorbent structure prior to compression and/or shaping of the absorbent structure into pledget. The absorbent structure may be rolled, folded, or otherwise manipulated into a blank prior to compression of the blank into a pledget.

The term "compression" refers herein to the process of pressing, squeezing, compacting, or otherwise manipulating the size, shape, and/or volume of a material to obtain an insertable tampon.

For example, a tampon blank can undergo compression to obtain a tampon having a vaginally insertable shape. The term "compressed" refers herein to the state of the material(s) subsequent to compression. Conversely, the term "uncompressed" refers herein to the state of the material(s) prior to compression. The term "compressible" is the ability of the material to undergo compression.

The term "cross-section" refers herein to either a plane that is orthogonal to a longitudinal axis (a "lateral cross-section") such as being orthogonal to the longitudinal axis of a tampon or being orthogonal to the longitudinal axis of the compression apparatus; or the term "cross-section" can also refer herein to a plane that is parallel with the longitudinal axis ("a longitudinal cross-section") such as being parallel to the longitudinal axis of the tampon or as being parallel to the longitudinal axis of the compression apparatus.

The term "digital tampon" refers herein to a tampon which is intended to be inserted into the vaginal cavity with the user's fingers and without the aid of an applicator. Thus, digital tampons are typically visible to the user prior to use rather than being housed in an applicator.

The term "folded" refers herein to the configuration of a blank that can be incidental to the lateral compaction of the absorbent structure of the blank or may purposefully occur prior to the compression step. Such a configuration can be readily recognizable, for example, when the absorbent material of the absorbent structure abruptly changes direction such that one part of the absorbent structure bends or lies over another part of the absorbent structure.

The term "generally cylindrical" refers herein to the usual shape of tampons as is well known in the art, but which also includes oblate or partially flattened cylinders, curved cylinders, and shapes which have varying cross-sectional areas (e.g., bottle shaped) along the longitudinal axis.

The term "longitudinal axis" refers herein to the axis running in the direction of the longest linear dimension of the tampon. For example, the longitudinal axis of a tampon is the axis which runs from the insertion end to the withdrawal end.

The term "outer surface" refers herein to the visible surface of the (compressed and/or shaped) tampon prior to use and/or expansion. At least part of the outer surface may be smooth or alternatively may have topographical features such as ribs, channels, a mesh pattern, or other topographical features.

The term "pledget" refers herein to a construction of an absorbent structure following compression of a blank.

The term "radial axis" refers herein to the axis that runs at right angles to the longitudinal axis of the tampon.

The term "rolled" refers herein to a configuration of the blank after winding the absorbent structure upon itself.

The term "tampon" refers herein to an absorbent structure that is inserted into the vaginal cavity for the absorption of body fluid therefrom or for the acute delivery of active materials, such as medicaments. A tampon blank may have been compressed to form a generally cylindrical tampon. While the tampon can be in a generally cylindrical configuration, other shapes are possible. These shapes can include, but are not limited to, having a lateral cross-section that can be described as rectangular, triangular, trapezoidal, semi-circular, hourglass, serpentine, or other suitable shapes. Tampons have an insertion end, a withdrawal end, a withdrawal element, a length, a width, a longitudinal axis, a radial axis, and an outer surface. The tampon's length can be measured from the insertion end to the withdrawal end along the longitudinal axis. A typical tampon can have a length from about 30 mm to about 60 mm. A tampon can be linear or non-linear in shape, such as, for example, curved along the longitudinal axis. A typical tampon can have a width from about 2 mm to about 30 mm. The width of the tampon, unless otherwise stated, corresponds to the measurement across the largest transverse cross-section along the length of the tampon.

The term "vaginal cavity" refers herein to the internal genitalia of the mammalian female in the pudendal region of the body. The term generally refers to the space located between the introitus of the vagina (sometimes referred to as the sphincter of the vagina or the hymeneal ring) and the cervix. The term does not include the interlabial space, the floor of the vestibule, or the externally visible genitalia.

Tampon:

The present disclosure is directed towards a tampon designed to be inserted above the introital region of a woman's vaginal cavity. The tampon is designed to function so as to intercept body fluids such as menses, blood, and other body fluids and prevent the body fluids from exiting the vaginal cavity. In the manufacture of a tampon, an absorbent structure composed of an absorbent material can be formed into a tampon blank. In various embodiments, a withdrawal element can be attached to the absorbent structure either before or after the absorbent structure is formed into a tampon blank. The tampon blank can then undergo a compression step which can result in the pledget of the tampon. The pledget, and resultant tampon, can have at least one linear channel and at least one non-linear channel.

Figure 1B:
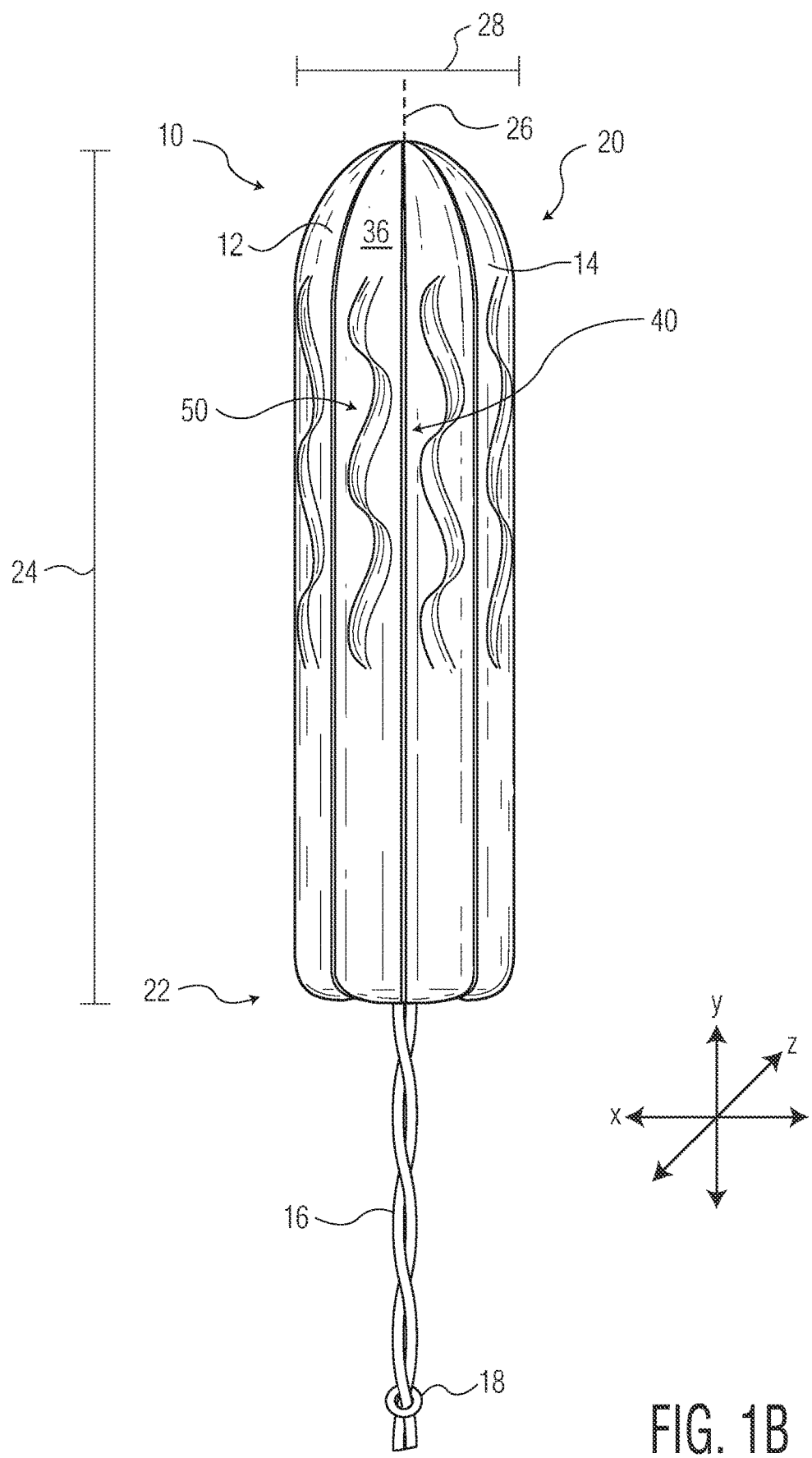
Figure 1C:
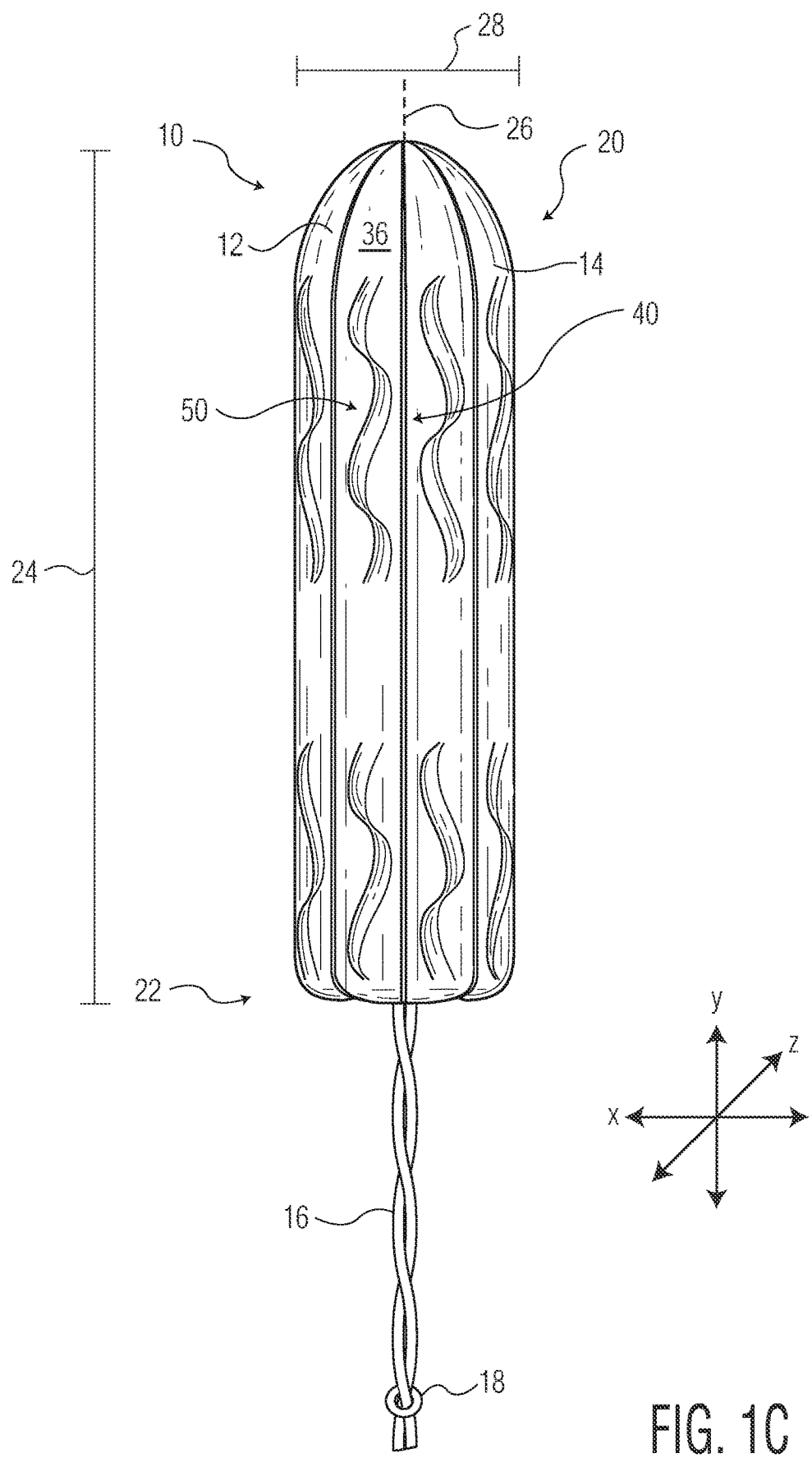

FIGS. 1A, 1B, and 1C illustrate side views of exemplary tampons 10. The tampon 10 can have a compressed, generally cylindrical shaped absorbent pledget 12 composed of an absorbent material 14 and a withdrawal element 16. In various embodiments, the withdrawal element 16 can have a knot 18 which can ensure that the withdrawal element 16 does not separate from the pledget 12. The tampon 10 can have a longitudinal direction (Y), a circumferential direction (X), and a radial depth direction (Z). In various embodiments, the generally cylindrical shape of the pledget 12 can have a lateral cross-section that is at least one of oval, circle, square, rectangle, or any other lateral cross-sectional shape known in the art. The tampon 10 can have an insertion end 20 and a withdrawal end 22. The tampon 10 can have a tampon length 24 wherein the tampon length 24 is the measurement of the tampon 10 along the longitudinal axis 26 originating at one end (insertion or withdrawal) of the tampon 10 and ending at the opposite end (insertion or withdrawal) of the tampon 10. In various embodiments, the tampon 10 can have a tampon length 24 from about 30 mm to about 60 mm. In various embodiments, the tampon 10 can have a compressed width 28, which unless otherwise stated herein, can correspond to the greatest lateral cross-sectional dimension along the longitudinal axis 26 of the tampon 10. In various embodiments, the tampon 10 can have a compressed width 28 prior to usage from about 2, 5, or 8 mm to about 10, 12, 14, 16, 20 or 30 mm. In various embodiments, the tampon 10 may be straight or non-linear in shape, such as curved along the longitudinal axis 26.

Figure 2A:
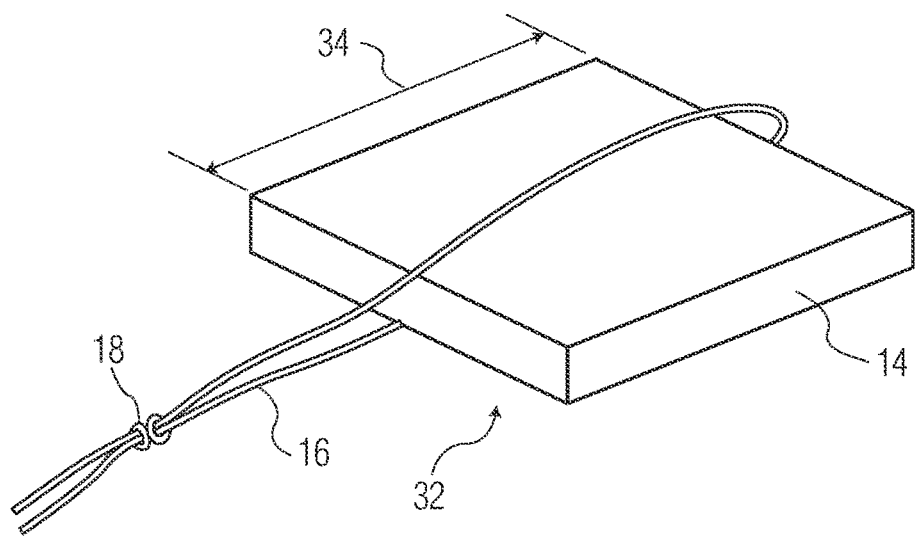
FIG. 2A is a perspective view of an exemplary embodiment of an absorbent structure.
Figure 2B:
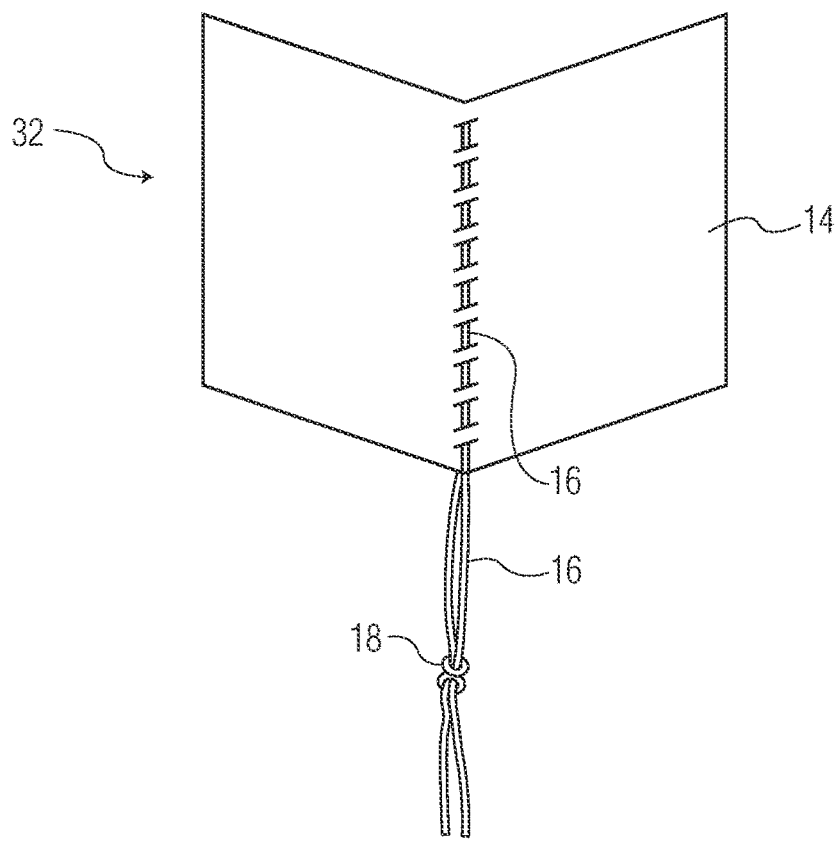
FIG. 2B is a top down view of an exemplary embodiment of an absorbent structure.

As noted above, the tampon 10 can have an absorbent pledget 12 which is formed via the compression of a tampon blank 30. The tampon blank 30 is formed, in turn, from an absorbent structure 32 which is composed of an absorbent material 14. FIG. 2A illustrates a perspective view of an exemplary embodiment of an absorbent structure 32 composed of absorbent material 14. The absorbent structure 32 illustrated in FIG. 2A is generally in the shape of a square. A withdrawal element 16 having a knot 18 is also associated with the absorbent structure 32. FIG. 2B illustrates a top down view of an exemplary embodiment of an absorbent structure 32 composed of absorbent material 14. The absorbent structure 32 illustrated in FIG. 2B has a generally chevron shape. A withdrawal element 16 having a knot 18 is also associated with the absorbent structure 32. It is to be understood that these two shapes, square and chevron, are illustrative and the absorbent structure 32 can have any shape, size, and thickness that can ultimately be compressed to form a tampon 10, such as, for example, tampon 10 in FIGS. 1A-1C. Non-limiting examples of the shape of an absorbent structure 32 can include, but are not limited to, oval, round, chevron, square, rectangular, and the like.

In an embodiment, the absorbent structure 32 can have a length dimension 34 from about 30 mm to about 80 mm. The length dimension 34 can be the linear measurement from the portion of the absorbent structure 32 which will ultimately form the insertion end 20 of the tampon 10 to the portion of the absorbent structure 32 which will ultimately form the withdrawal 22 end of the tampon 10. In an embodiment, the basis weight of the absorbent structure 32 can range from about 15, 20, 25, 50, 75, 90, 100, 110, 120, 135, or 150 gsm to about 1,000, 1,100, 1,200, 1,300, 1,400, or 1,500 gsm.

The absorbent structure 32 can have a single layer of absorbent material 14 or the absorbent structure 32 can be a laminar structure that can have individual distinct layers of absorbent material 14. In an embodiment in which the absorbent structure 32 has a laminar structure, the layers can be formed from a single absorbent material and/or from different absorbent materials.

The absorbent material 14 of the absorbent structure 32 can be absorbent fibrous material. Such absorbent material 14 can include, but is not limited to, natural and synthetic fibers such as, but not limited to, polyester, acetate, nylon, cellulosic fibers such as wood pulp, cotton, rayon, viscose, LYOCELL® such as from Lenzig Company of Austria, or mixtures of these or other cellulosic fibers. Natural fibers can include, but are not limited to, wool, cotton, flax, hemp, and wood pulp. Wood pulps can include, but are not limited to, standard softwood fluffing grade such as CR-1654 (US Alliance Pulp Mills, Coosa, Ala.). Pulp may be modified in order to enhance the inherent characteristics of the fibers and their processability, such as, for example, by crimping, curling, and/or stiffening. The absorbent material 14 can include any suitable blend of fibers. For example, the absorbent material 14 can be formed from cellulose fibers such as cotton and rayon. The absorbent fibers can be 100 wt % cotton, 100 wt % rayon, or as blend of cotton and rayon.

In various embodiments, the absorbent fibers can have a staple length of from about 5, 10, 15 or 20 mm to about 30, 40, or 50 mm. In various embodiments, the absorbent fibers can have a fiber size of from about 15 microns to about 28 microns. In various embodiments, the absorbent fibers can have a denier of from about 1 or 2 to about 6. Denier is a unit of fineness of yarn based on a standard of 50 milligrams (mg) for 450 meters of yarn. In various embodiments, the absorbent fibers can have a circular, bi-lobal, or tri-lobal cross-sectional configuration or any other configuration known to those skilled in the art. A bi-lobal configuration can have a cross-sectional profile which can look like a dog bone while a tri-lobal configuration can have a cross-sectional profile which can look like a "Y". In various embodiments, the absorbent fibers can be bleached. In various embodiments, the absorbent fibers can have a color.

In various embodiments, the absorbent structure 32 can contain fibers such as binder fibers. In an embodiment, the binder fibers can have a fiber component which will bond or fuse to other fibers in the absorbent structure 32. Binder fibers can be natural fibers or synthetic fibers. Synthetic fibers include, but are not limited to, those made from polyolefins, polyamides, polyesters, rayon, acrylics, viscose, superabsorbents, LYOCELL® regenerated cellulose, and any other suitable synthetic fiber known to those skilled in the art. The fibers can be treated by conventional compositions and/or processes to enable or enhance wettability.

In various embodiments, the absorbent structure 32 can have any suitable combination and ratio of fibers. In an embodiment, the absorbent structure 32 can include from about 70 or 80 wt % to about 90 or 95 wt % absorbent fibers and from about 5 or 10 wt % to about 20 or 30 wt % binder fibers. In various embodiments, the absorbent structure 32 can include about 85 wt % absorbent fibers and about 15 wt % binder fibers. In various embodiments, the absorbent structure 32 can include from about 80 to about 90 wt % tri-lobal viscose rayon fibers and from about 10 to about 20 wt % bicomponent binder fibers. In various embodiments, the absorbent structure 32 can include 85 wt % tri-lobal viscose rayon fibers and about 15 wt % bicomponent binder fibers. In various embodiments, the absorbent structure 32 can include greater than about 70, 80, 90, 95, 97 or 99 wt % absorbent fibers.

Various methods known to those skilled in the art can be used to prepare the absorbent structure 32. Such methods can include, but are not limited to, airlaying, carding, wetlaying, needlepunching, mechanical entanglement, hydroentangling, and any other known method deemed suitable by one of ordinary skill. In various embodiments, a bonded carded web can be made from staple fibers. In such embodiments, the fibers can be longer than about 20, 30, or 35 mm. The fibers can be purchased in bales which can be placed in a picker to separate the fibers. The fibers can then be sent through a combing or carding unit, which can further break apart and align the fibers in the machine direction to form a generally machine direction-oriented fibrous nonwoven web. Once the web is formed, it can then be bonded by one or more of several known bonding methods, such as air bonding or pattern bonding. In various embodiments, a dry laid web can be made from staple fibers. In such embodiments, the fibers can be about 20 mm or longer. In dry laying, fibers or tufts of fibers of a first type (e.g., absorbent fibers and/or binder fibers) can be fed to a first rotating vacuum drum and fibers or tufts of fibers of a second type (e.g., absorbent fibers and/or binder fibers) can be fed to a second rotating vacuum drum. The fibers can then be laid down by suction to form mats of fibers. The mats of fibers can be doffed from the vacuum drums and combed via rotating lickerins. The lickerins can have peripheral teeth which can comb the fibers from the mat. The combed fibers can be doffed from the lickerins via centrifugal force and placed into a fiber mixing and expansion chamber. The mixed fibers can be placed on a vacuum screen to form a random fiber web comprising the first and second type fibers. The flow and velocity of each independent fiber stream can be controlled to provide the desired quantity of each fiber type.

In various embodiments in which binder fibers are present, the binder fibers can be activated to create a three-dimensional fiber matrix. In such an embodiment, the activation can be completed by any suitable heating step including, but not limited to, conventional heating, through air heating, superheated steam, microwave heating, radiant heating, radio frequency heating, and the like, and combinations thereof. In various embodiments, the activation can be followed by a cooling step which can utilize any suitable means for reducing the temperature of the absorbent structure 32.

In various embodiments, a cover can be provided as known to one of ordinary skill in the art. As used herein, the term "cover" relates to materials that are in communication with and cover or enclose surfaces, such as, for example, an outer surface 36 of the tampon 10. The cover may be beneficial in assuring that the fibers of the tampon 10 do not directly contact the inner walls of the woman's vaginal cavity. Additionally, the cover can reduce the ability of portions (e.g., fibers and the like) from becoming separated from the tampon 10 and being left behind upon removal of the tampon 10 from the woman's vaginal cavity. In various embodiments, the cover can be a fluid-permeable cover. By "fluid-permeable" it is meant that body fluid is able to pass through the cover. The cover can be hydrophobic or hydrophilic. In various embodiments in which the cover is hydrophobic, the cover can be treated with a surfactant or other material to make it hydrophilic.

In various embodiments, the cover can be formed from nonwoven materials or aperture films. The nonwoven materials can include, but are not limited to, materials such as natural fibers, synthetic fibers, or blends of natural and synthetic fibers. Natural fibers can include, but are not limited to, rayon, cotton, wood pulp, flax, and hemp. Synthetic fibers can include, but are not limited to, fibers such as polyester, polyolefin, nylon, polypropylene, polyethylene, polyacrylic, vinyl polyacetate, polyacrylate, cellulose acetate, or bicomponent fibers, such as bicomponent polyethylene and polypropylene fibers. The cover can be made by any number of suitable techniques such as, for example, being spunbond, carded, hydroentangled, thermally bonded, and resin bonded. In various embodiments, the cover can be a 12 gsm smooth calendared material made from bicomponent, polyester sheath and polyethylene core, fibers such as Sawabond 4189 available from Sandler AG, Schwarzenbach, Germany. In various embodiments, the cover can be formed from an aperture thermoplastic film having either a two-dimensional or a three-dimensional thickness. In various embodiments, the cover can be bleached. In various embodiments, the cover can have a color.

In various embodiments, the absorbent structure 32 may be attached to a withdrawal element 16. The withdrawal element 16 may be attached to the absorbent structure 32 in any suitable manner as known to one of ordinary skill in the art. A knot 18 can be formed near the free ends of the withdrawal element 16 to assure that the withdrawal element 16 does not separate from the absorbent structure 32. The knot 18 can also serve to prevent fraying of the withdrawal element 16 and to provide a place where a woman can grasp the withdrawal element 16 when she is ready to remove the tampon 10 from her vaginal cavity. The withdrawal element 16 can be constructed from various types of threads or ribbons. A thread or ribbon can be made from 100% cotton fibers and/or other materials in whole or in part. The withdrawal element 16 can have any suitable length and/or the withdrawal element 16 can be dyed and/or treated with an anti-wicking agent, such as wax, before being attached to the absorbent structure 32.

Figure 3A:
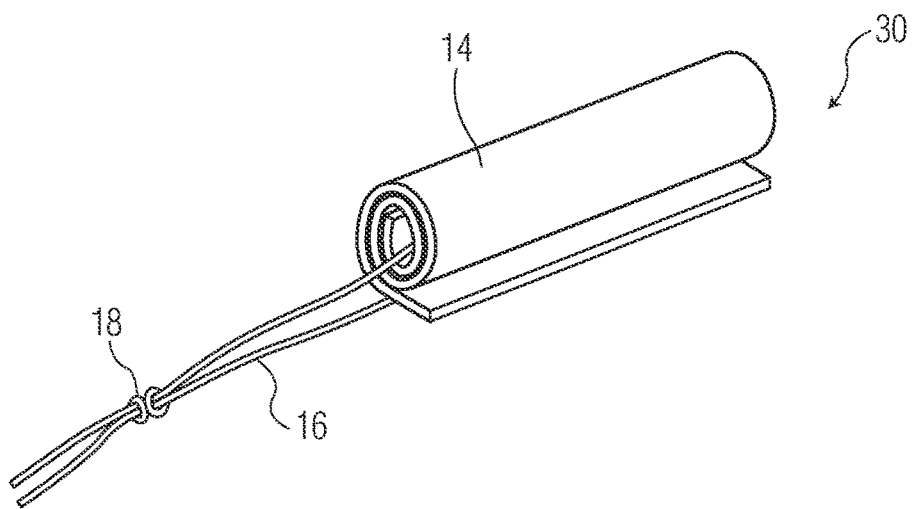
FIGS. 3A and 3B are perspective views of exemplary embodiments of tampon blanks.
Figure 3B:
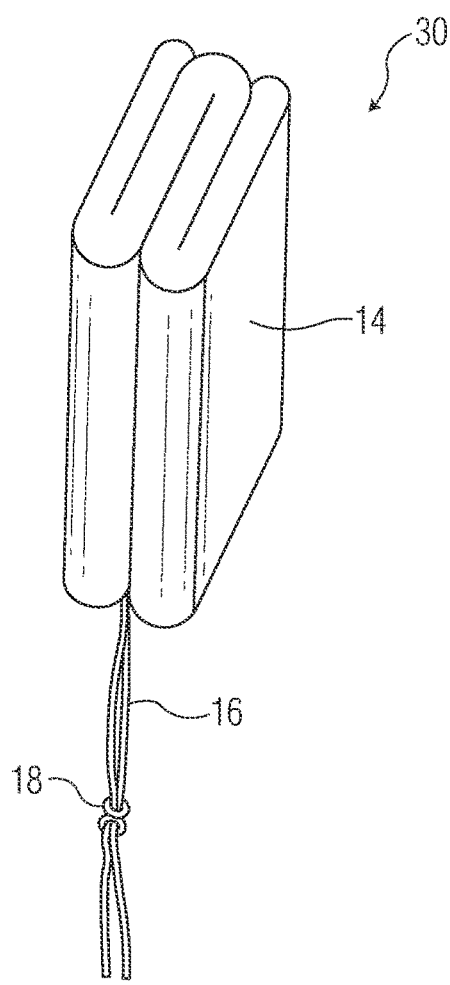

The absorbent structure 32 can be rolled, stacked, folded, or otherwise manipulated into a tampon blank 30 before compressing the tampon blank 30 into a pledget 12. FIG. 3A is an illustration of a perspective view of an example of a rolled tampon blank 30, such as a radially wound tampon blank 30. FIG. 3B is an illustration of a perspective view of an example of a folded tampon blank 30. It is to be understood that radially wound and folded configurations are illustrative and additional tampon blank 30 and pledget 12 configurations are possible. For example, suitable menstrual tampons may include "cup" shaped tampon blanks and pledgets like those disclosed in U.S. Publication No. 2008/0287902 to Edgett and U.S. Pat. No. 2,330,257 to Bailey; "accordion" or "W-folded" tampon blanks and pledgets like those disclosed in U.S. Pat. No. 6,837,882 to Agyapong; "radially wound" tampon blanks and pledgets like those disclosed in U.S. Pat. No. 6,310,269 to Friese; "sausage" type or "wad" tampon blanks and pledgets like those disclosed in U.S. Pat. No. 2,464,310 to Harwood; "M-folded" tampon blanks and pledgets like those disclosed in U.S. Pat. No. 6,039,716 to Jessup; "stacked" tampon blanks and pledgets like those disclosed in U.S. 2008/0132868 to Jorgensen; or "bag" type tampon blanks and pledgets like those disclosed in U.S. Pat. No. 3,815,601 to Schaefer. A suitable method for making "radial wound" tampon blanks and pledgets is disclosed in U.S. Pat. No. 4,816,100 to Friese. Suitable methods for making "W-folded" tampon blanks and pledgets are disclosed in U.S. Pat. No. 6,740,070 to Agyapong; U.S. Pat. No. 7,677,189 to Kondo; and U.S. 2010/0114054 to Mueller. A suitable method for making "cup" tampon blanks and pledgets and "stacked" tampon blanks and pledgets is disclosed in U.S. 2008/0132868 to Jorgensen.

In various embodiments, the tampon blank 30 can be compressed into a pledget 12. The tampon blank 30 may be compressed any suitable amount. For example, the tampon blank 30 can be compressed at least about 25%, 50%, or 75% of the initial dimensions. For example, a tampon blank 30 can be reduced in diameter to approximately ¼ of the original uncompressed diameter. The lateral cross-sectional configuration of the resultant tampon 10 may be circular, ovular, elliptical, rectangular, hexagonal, or any other suitable shape.

Referring to FIGS. 1A-1C, following compression of the tampon blank 30 to form the pledget 12, the pledget 12 and the resultant tampon 10 can have at least one linear channel 40 and at least one non-linear channel 50. Without being bound by theory, a tampon which does not have any type of channel and, therefore, a tampon with a smooth outer surface, can have difficulty in absorbing body fluid fast enough as the body fluid can simply move over the smooth surface of the tampon and leak from the body of the user of the tampon. Providing a tampon with a linear channel 40 and a non-linear channel 50 can provide columnar strength and can create a void space area which is below the outer surface 36 of the tampon 10 and within which the body fluid can accumulate and be absorbed by the tampon 10 rather than simply passing over a smooth outer surface of a tampon and leaking from the body of the user of the tampon.

Referring to FIGS. 1A-1C, and 4, a linear channel 40 is a straight channel which can extend in the longitudinal direction (Y) of the tampon 10. The linear channel 40 has a uniform dimension in the circumferential direction (X) at the outer surface 36 of the tampon 10 and referring to FIGS. 5A-5L a uniform lateral cross section in the radial depth direction (Z) as the linear channel 40 extends in the longitudinal direction (Y) of the tampon 10. In various embodiments, such as, for example, as illustrated in FIGS. 1A-1C, a linear channel 40 can extend the total tampon length 24 from the insertion end 20 to the withdrawal end 22.

In various embodiments, a linear channel 40 can be defined by an opposing pair of outer surface edges 42 and an opposing pair of channel sidewalls 44. Each of the channel sidewalls 44 can extend from each of the outer surface edges 42, respectively, in a direction towards the longitudinal axis 26 of the tampon 10. The channel sidewalls 44 can extend any depth into the tampon 10 as desired. The channel sidewalls 44 can join together at an inner surface 46 of the linear channel 40 wherein the inner surface 46 defines the bottom of the linear channel 40. The inner surface 46 of the linear channel 40 forms a portion of the exterior of the tampon 10, however, the inner surface 46 of the linear channel 40 is at a depth below the outer surface 36 of the tampon 10. In various embodiments, the depth of the linear channel 40, as measured from the outer surface 36 to the inner surface 46, can be from about 0.1, 0.2, 0.4, 0.6, 0.8, 1, 1.2, 1.4, 1.6, 1.8 or 2 mm to about 2.2, 2.4, 2.6, 2.8 or 3 mm. The linear channel 40 can also have a width dimension 48 as measured as the distance between the opposing pair of outer surface edges 42. In various embodiments, the width dimension 48 of the linear channel 40 can be from about 0.1, 0.2, 0.4, 0.6, 0.8, 1, 1.2, or 1.4 mm to about 1.6, 1.8 or 2 mm.

The inner surface 46 of the linear channel 40 can be of any shape and configuration as desired. For example, referring to FIGS. 5A-5L, the inner surface 46 of the linear channel 40 can be a sharp angle between the two channel sidewalls 44 such as, for example, in a V-configuration (FIGS. 5A and 5H), can be a rounded curve configuration between the two channel sidewalls 44 such as, for example, in a rounded-V configuration (FIGS. 5B, 5G, and 5L), can have an arcuate shape and more width in the circumferential direction (X) of the tampon than a rounded-V configuration such as, for example, a U-configuration (FIGS. 5C and 5K), can have a flat inner surface 46 while at least one of the sidewalls 44 remain at an angle to the longitudinal axis 26 of the tampon 10, such as, for example, as can be seen in FIGS. 5D, 5E, 5F, 5I, and 5J. It is to be understood that these are non-limiting examples of the inner surface 46 configuration and other configurations are possible as deemed suitable by one of ordinary skill.

Referring to FIGS. 1A-1C, and 4, a non-linear channel 50 can extend in at least a portion of the longitudinal direction (Y) of the tampon 10. In various embodiments, such as illustrated in FIG. 1A, a non-linear channel 50 can extend the total tampon length 24 from the insertion end 20 to the withdrawal end 22. In various embodiments, such as illustrated in FIG. 1B, a non-linear channel 50 can extend a portion of the tampon length 24. For example, as illustrated in FIG. 1B a non-linear channel 50 can extend from the insertion end 20 to approximately the middle of the tampon length 24 of the tampon 10. In various embodiments in which a non-linear channel 50 extends only a portion of the tampon length 24 of the tampon 10, a non-linear channel 50 can extend from the insertion end 20 to the middle of the tampon length 24 of the tampon 10, from the withdrawal end 22 to the middle of the tampon length 24 of the tampon 10, or can be present in the middle third of the tampon 10 without extending to either of the insertion end 20 or withdrawal end 22. In various embodiments in which a non-linear channel 50 extends only a portion of the tampon length 24 of the tampon 10, the tampon 10 can have multiple non-linear channels 50 present in a common region of the tampon 10 such as, for example, a tampon 10 can have a first non-linear channel 50 in a spaced apart relationship in the longitudinal direction (Y) from a second non-linear channel 50. For example, as illustrated in FIG. 1C, a tampon 10 can have a first non-linear channel 50 present at the insertion end 20 and extending in the longitudinal direction (Y) towards the middle of the tampon length 24 of the tampon 10 and a second non-linear channel 50 present at the withdrawal end 22 of the tampon and extending towards the middle of the tampon length 24 of the tampon 10 wherein the first non-linear channel 50 and the second non-linear channel 50 are present in the same longitudinal plane of the tampon 10 and separated from each other by a distance in the longitudinal direction (Y).

Referring to FIGS. 1A-1C, and 4, in various embodiments, a non-linear channel 50 can be defined by an opposing pair of outer surface edges 52 and an opposing pair of channel sidewalls 54. Each of the channel sidewalls 54 can extend from each of the outer surface edges 52, respectively, in a direction towards the longitudinal axis 26 of the tampon 10. In various embodiments, a non-linear channel 50 can undulate in the radial depth direction (Z) as the non-linear channel 50 extends in at least a portion of the longitudinal direction (Y) of the tampon 10. In various embodiments, a non-linear channel 50 can undulate in the circumferential direction (X) as the non-linear channel 50 extends in at least a portion of the longitudinal direction (Y) of the tampon 10. In various embodiments, a non-linear channel 50 can undulate in the radial depth direction (Z) as well as in the circumferential direction (X) as the non-linear channel 50 extends in at least a portion of the longitudinal direction (Y) of the tampon 10.

In various embodiments, a width between the channel surface edges 52 of a non-linear channel 50, measured at the outer surface 36 of the tampon 10, can be uniform in a least a portion of the non-linear channel 50. In various embodiments, a width between the channel surface edges 52 of a non-linear channel 50, measured at the outer surface 36 of the tampon 10, can be uniform throughout the extent of the non-linear channel 50. In various embodiments, a width between the channel surface edges 52 of a non-linear channel 50, measured at the outer surface 36 of the tampon 10, can vary in at least a portion of the non-linear channel 50. In various embodiments, a width between the channel surface edges 52 of a non-linear channel 50, measured at the outer surface 36 of the tampon 10, can vary throughout the extent of the non-linear channel 50.

Figure 5C:
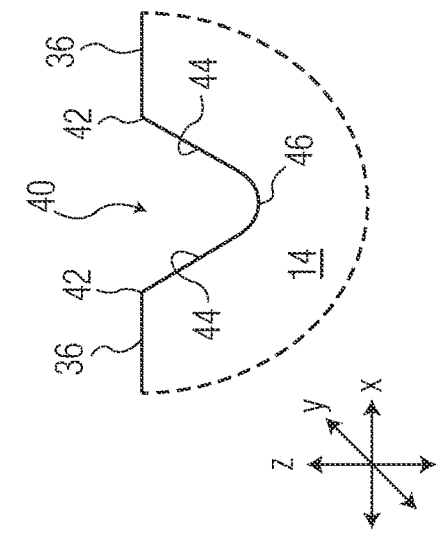
FIGS. 5A-5L are lateral cross-sections of illustrative exemplary embodiments of the shape of an inner surface of a linear channel.
Figure 5F:
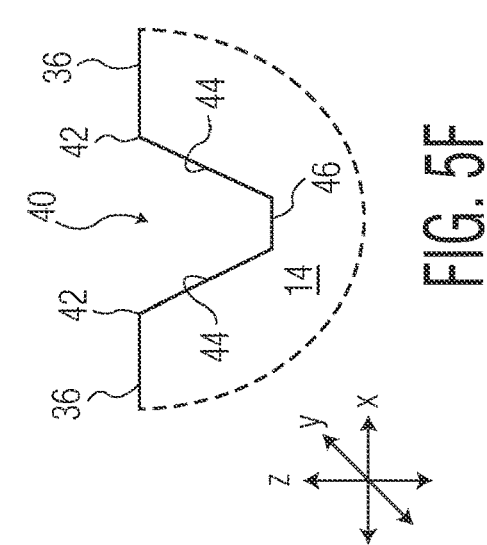
Figure 5B:
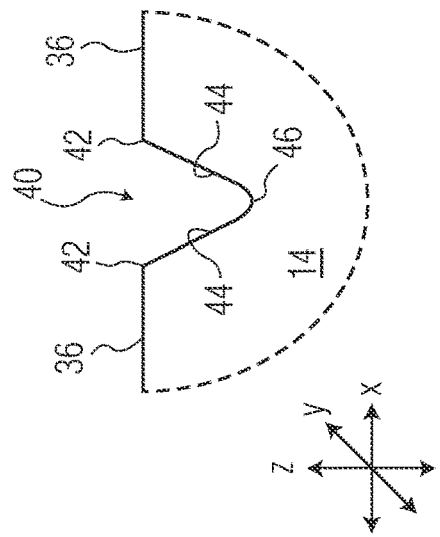
Figure 5E:
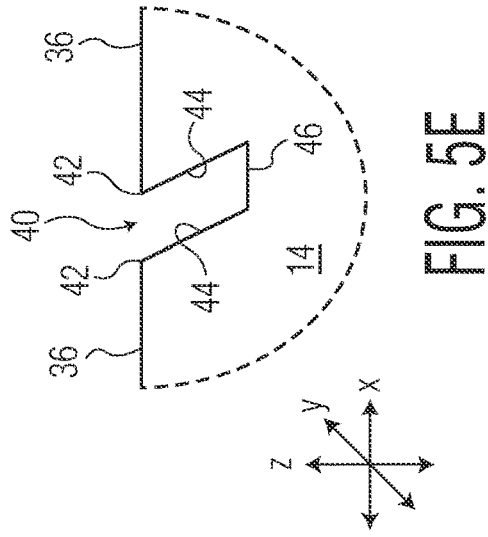
Figure 5A:
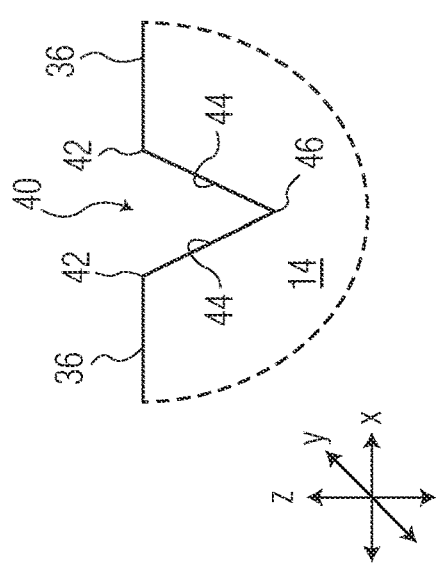
Figure 5D:
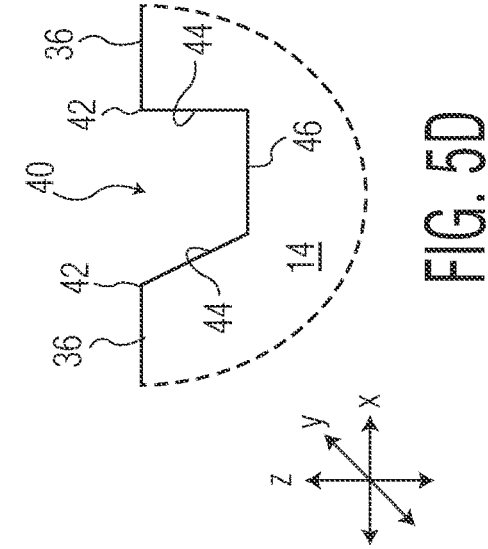
Figure 5G:
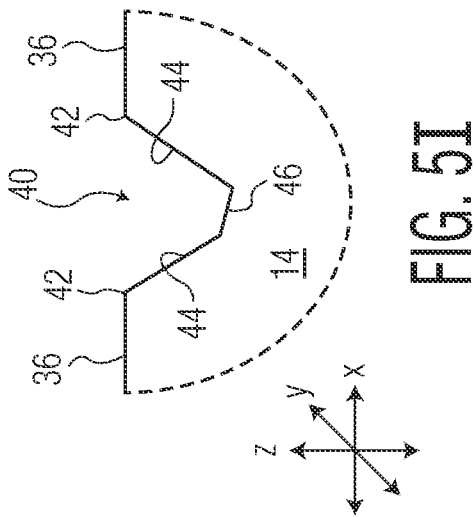
Figure 5H:
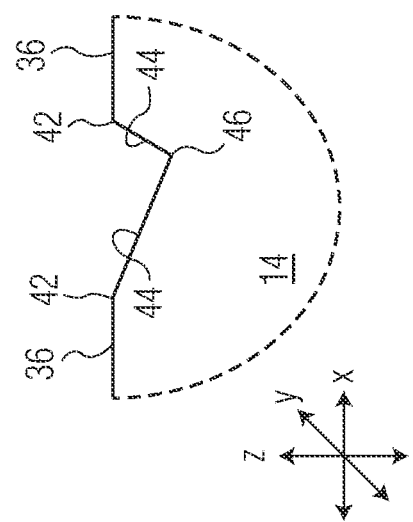
Figure 5I:
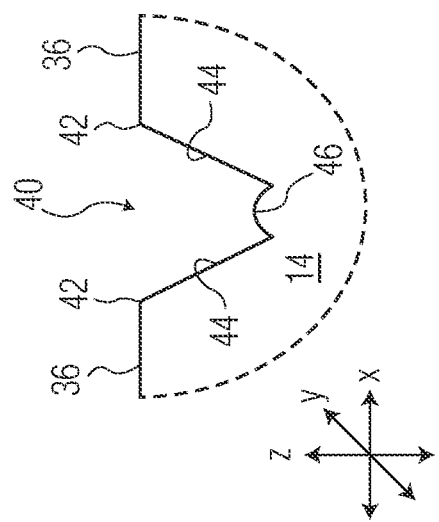
Figure 5J:
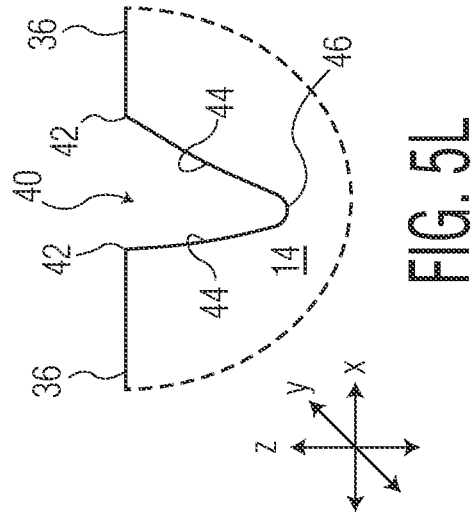
Figure 5K:
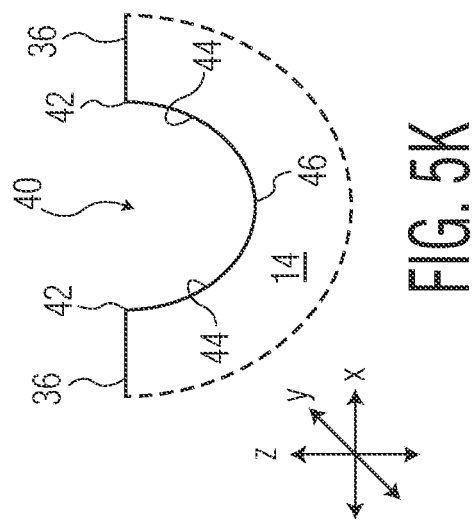
Figure 5L:
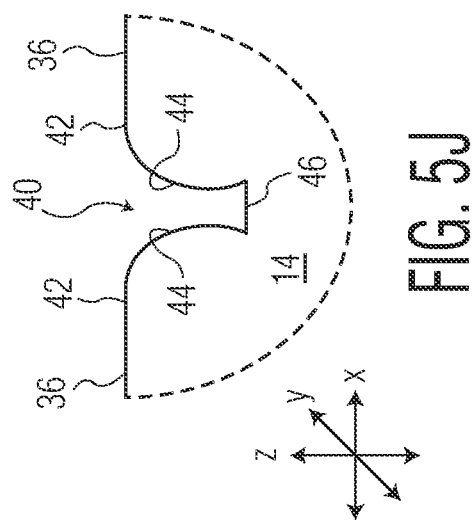
Figure 6:
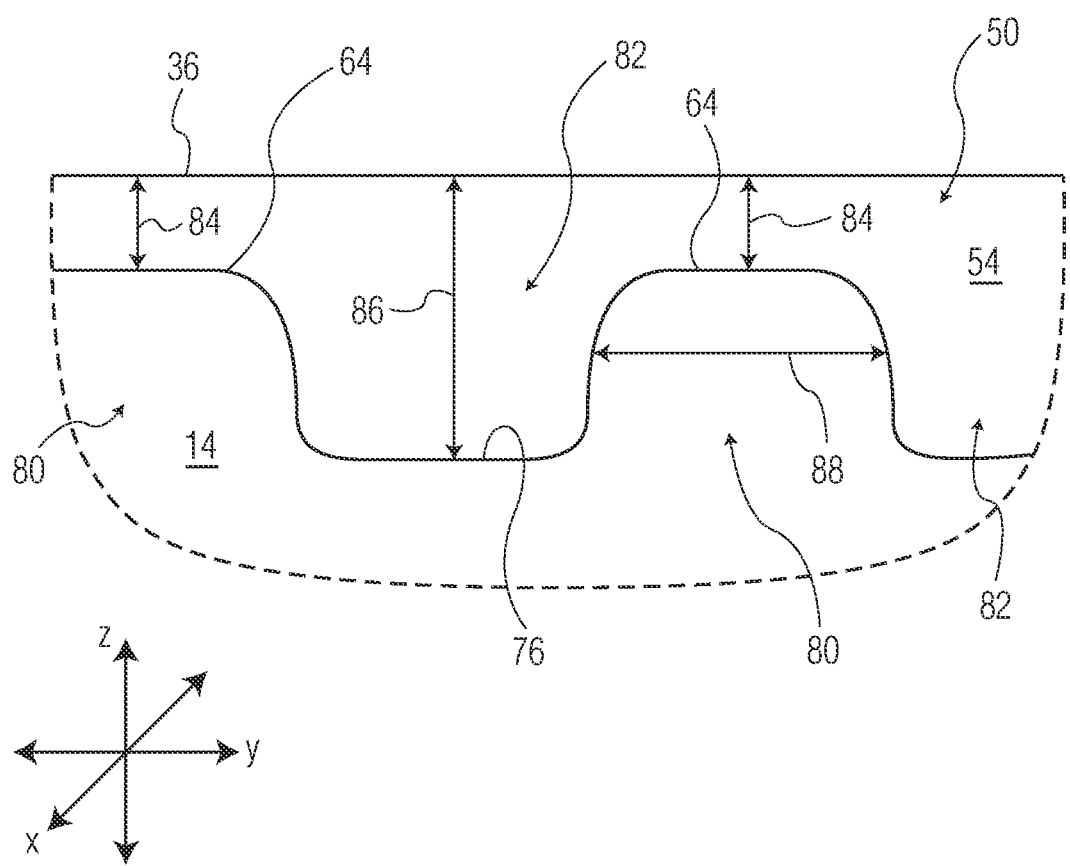
FIG. 6 is a longitudinal cross-section of an illustration of an exemplary embodiment of a non-linear channel.

Referring to FIG. 6, in various embodiments, a non-linear channel 50 can be defined by an undulation in the radial depth direction (Z) as the non-linear channel 50 extends in at least a portion of the longitudinal direction (Y) of the tampon 10. The sidewalls 54 of the non-linear channel 50 can join together at an inner surface wherein the inner surface defines the bottom of the non-linear channel 50. The undulation in the radial depth direction (Z) can result in a portion of the inner surface, such as first portion 64, defining a crest 80 and a portion of the inner surface, such as second portion 76, defining a trough 82. In various embodiments, a non-linear channel 50 can have at least 1, 2, 3, 4, 5, 6, 7, 8, 9, or 10 crests 80 and can have at least 1, 2, 3, 4, 5, 6, 7, 8, 9, or 10 troughs 82. In an embodiment, a non-linear channel 50 can have at least 2 crests 80 and 1 trough 82. In an embodiment, a non-linear channel 50 can have at least 1 crest 80 and 2 troughs 82. The non-linear channel 50, therefore, can have a variable depth dimension below the outer surface 36 of the tampon 10. The variable depth dimension below the outer surface 36 of the tampon 10 can result in troughs 82 where body fluid can pool while awaiting absorption by the tampon 10 and the crests 80 can provide barrier to movement of the body fluid out of the troughs 82 in the longitudinal direction (Y) of the tampon 10. In various embodiments, the non-linear channel 50 can have a pattern of crests 80 and troughs 82 wherein the crests 80 have a first depth dimension 84 below the outer surface 36 of the tampon 10 and the troughs 82 have a second depth dimension 86 below the outer surface 36 of the tampon 10. The first depth dimension 84 is different from the second depth dimension 86. In various embodiments, the first depth dimension 84 of a crest 80, as measured at the midpoint of the crest 80, of the non-linear channel 50 is from about 0.25, 0.3, 0.35 or 0.4 mm to about 0.45, 0.5, 0.55, 0.6, 0.65, 0.7, or 0.75 mm. In various embodiments, the second depth dimension 86 of a trough 82, as measured at the midpoint of the trough 82, of the non-linear channel 50 is from about 0.8, 0.85, 0.9, 0.95, or 1.0 mm to about 1.05, 1.1, 1.15, 1.2, 1.25, 1.3, or 1.35 mm. The first depth dimension 84 and the second depth dimension 86 are measured at the middle of the respective crest 80 and trough 82 and from the outer surface 36 of the tampon 10 to the respective first portion 64 of the inner surface and the second portion 76 of the inner surface. In various embodiments, the troughs 82 of the non-linear channel 50 can be separated from each other by a distance 88 of less than about 8, 7.6, 7, 6.6, 6, 5.6, or 5 mm. In various embodiments, as the non-linear channel 50 undulates in the radial depth direction (Z), the width between the between the channel surface edges 52, as measured at the outer surface 36 of the tampon 10, can be uniform. In various embodiments, as the non-linear channel 50 undulates in the radial depth direction (Z), the width between the channel surface edges 52, as measured at the outer surface 36 of the tampon 10, can be varied. In various embodiments, the width between the channel surface edges 52, as measured at the outer surface 36 of the tampon 10, can be from about 0.35, 0.4, 0.45, 0.5, 0.55, 0.6, 0.65, 0.7, 0.75, or 0.8 mm to about 0.85, 0.9, 0.95, 1, 1.05, 1.1, 1.15, 1.2, 1.25, 1.3, 1.35, 1.4, 1.5, 1.75, 2.0, 2.5, 3.0, 3.5, 4.0, 5.0, or 6.0 mm. The first portion 64 of the inner surface and the second portion 76 of the inner surface can be of any shape and configuration as desired. For example, the first portion 64 of the inner surface and the second portion 76 of the inner surface can be any of the shapes and configuration as described for the inner surface 46 of the linear channel 40, such as described and illustrated in FIGS. 5A-5L. It is to be understood that these are non-limiting examples of configuration of inner surfaces and other configuration are possible as deemed suitable by one of ordinary skill.

Figure 13:
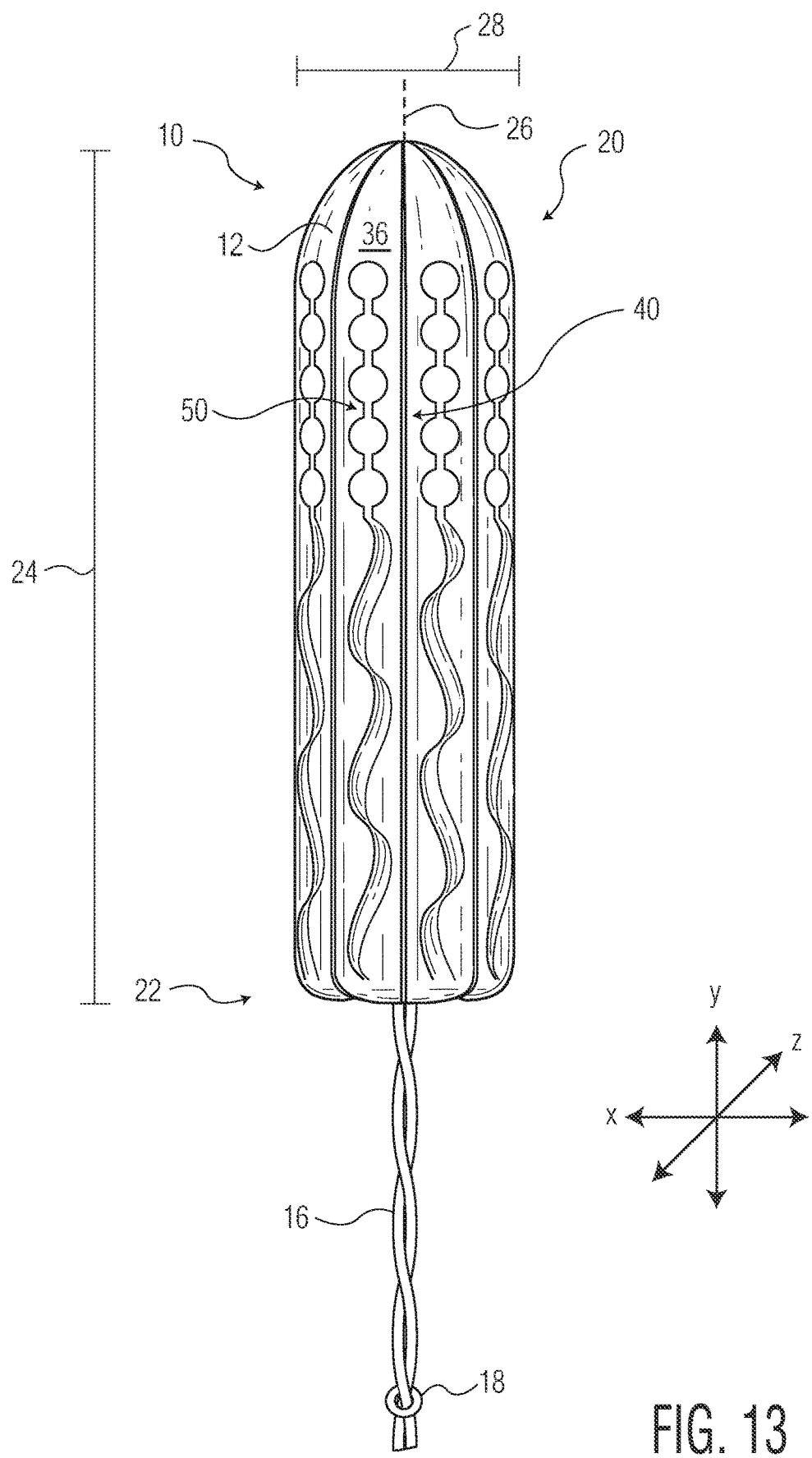
FIG. 13 is a side view of an exemplary embodiment of a tampon.

In various embodiments, referring to FIGS. 1A-1C, and 4, the non-linear channel 50 can be defined by an undulation in the circumferential direction (X) as the non-linear channel 50 extends in at least a portion of the longitudinal direction (Y) of the tampon 10. In various embodiments, the undulations in the circumferential direction (X) of a non-linear channel 50 can be defined by the sidewalls 54 of the non-linear channel 50 moving back-and-forth (i.e., to the left-and-right) in the circumferential direction (X) in a congruent manner with each other. In other words, each of the sidewalls 54 of a non-linear channel 50 resemble each other (such as can be seen in FIGS. 1A-1C, and 4). In various embodiments, the undulations in the circumferential direction (X) of a non-linear channel 50 can be defined by the sidewalls 54 of the non-linear channel 50 moving back-and-forth (i.e., to the left-and-right) in the circumferential direction (X) in a non-congruent manner with each other. In other words, each of the sidewalls 54 of a non-linear channel 50 are mirror images of each other. In various embodiments, a non-linear channel 50 can have a first portion in which the sidewalls 54 are congruent with each other and can have a second portion in which the sidewalls 54 are not congruent with each other (such as can be seen in FIG. 13). The undulations in the circumferential direction (X) can provide a back-and-forth pathway for the body fluid to follow. The change in direction of the pathway can slow the movement of the body fluid and can enable more body fluid to be absorbed by the tampon 10. As the tampon 10 can have at least one linear channel 40, a non-linear channel 50 which can undulate in the circumferential direction (X) does not intersect the linear channel 40 of the tampon 10.

In various embodiments, as the non-linear channel 50 undulates in the circumferential direction (X) of the tampon 10, a width between the channel surface edges 52, as measured at the outer surface 36 of the tampon 10, of the non-linear channel 50 can be uniform. In such embodiments, a width between the channel surface edges 52 of the non-linear channel 50, as measured at the outer surface 36 of the tampon 10, can be from about 0.35, 0.4, 0.45, 0.5, 0.55, 0.6, 0.65, 0.7, 0.75, or 0.8, mm to about 0.85, 0.9, 0.95, 1, 1.05, 1.1, 1.15, 1.2, 1.25, 1.3, 1.35, 1.4, 1.5, 1.75, 2.0, 2.5, 3.0, 3.5, 4.0, 5.0, or 6.0 mm. In various embodiments, as the non-linear channel 50 undulates in the circumferential direction (X) of the tampon 10, a width between the channel surface edges 52, as measured at the outer surface 36 of the tampon 10, of the non-linear channel 50 can vary as is illustrated in FIGS. 1A-1C, and 4. In such embodiments in which a non-linear channel 50 has a variable width, a non-linear channel 50 can have a first width 62 between the channel surface edges 52, as measured at the outer surface 36 of the tampon 10, from about 0.35, 0.4, 0.45, 0.5, 0.55, 0.6, 0.65, 0.7, 0.75, or 0.8, mm to about 0.85, 0.9, 0.95, 1, 1.05, 1.1, 1.15, 1.2, 1.25, 1.3, 1.35, 1.4, 1.5, 1.75, 2.0, 2.5, 3.0, 3.5, 4.0, 5.0, or 6.0 mm and the non-linear channel 50 can have a second width 74 between the channel sidewalls 54, as measured at the outer surface 36 of the tampon 10, from about 0.35, 0.4, 0.45, 0.5, 0.55, 0.6, 0.65, 0.7, 0.75, or 0.8, mm to about 0.85, 0.9, 0.95, 1, 1.05, 1.1, 1.15, 1.2, 1.25, 1.3, 1.35, 1.4, 1.5, 1.75, 2.0, 2.5, 3.0, 3.5, 4.0, 5.0, or 6.0 mm wherein the first width 62 and the second width 74 are not the same. The sidewalls 54 of the non-linear channel 50 can join together at an inner surface which is below the outer surface 36 of the tampon 10 and forms the bottom of the non-linear channel 50. The inner surface can be of any shape and configuration as desired. For example, the sidewalls 54 of the non-linear channel 50 can be perpendicular to the second portion of the inner surface 76 or the sidewalls 54 of the non-linear channel 50 can be oblique to the second portion of the inner surface 76 and for example can be any of the shapes and configuration as described for the inner surface 46 of the linear channel 40, such as described and illustrated in FIGS. 5A-5L. It is to be understood that these are non-limiting examples of configuration of inner surfaces and other configuration are possible as deemed suitable by one of ordinary skill.

In various embodiments, a non-linear channel 50 can undulate in the circumferential direction (X) as well as the radial depth direction (Z) as the non-linear channel 50 extends in at least a portion of the longitudinal direction (Y) of the tampon 10. A non-linear channel 50 having undulations in both the circumferential direction (X) and the radial depth direction (Z) can provide a benefit of not only creating a pathway for the body fluid to follow, but creating a tortuous pathway for the body fluid to follow in the longitudinal direction (Y) of the tampon 10 as the body fluid is following a pathway in both a left and right movement and an up and down movement. Such a tortuous pathway created by the non-linear channel 50, while providing a void space for the accumulation of the body fluid, can slow the movement of the body fluid through the non-linear channel 50 in the longitudinal direction (Y) of the tampon 10.

Figure 4:
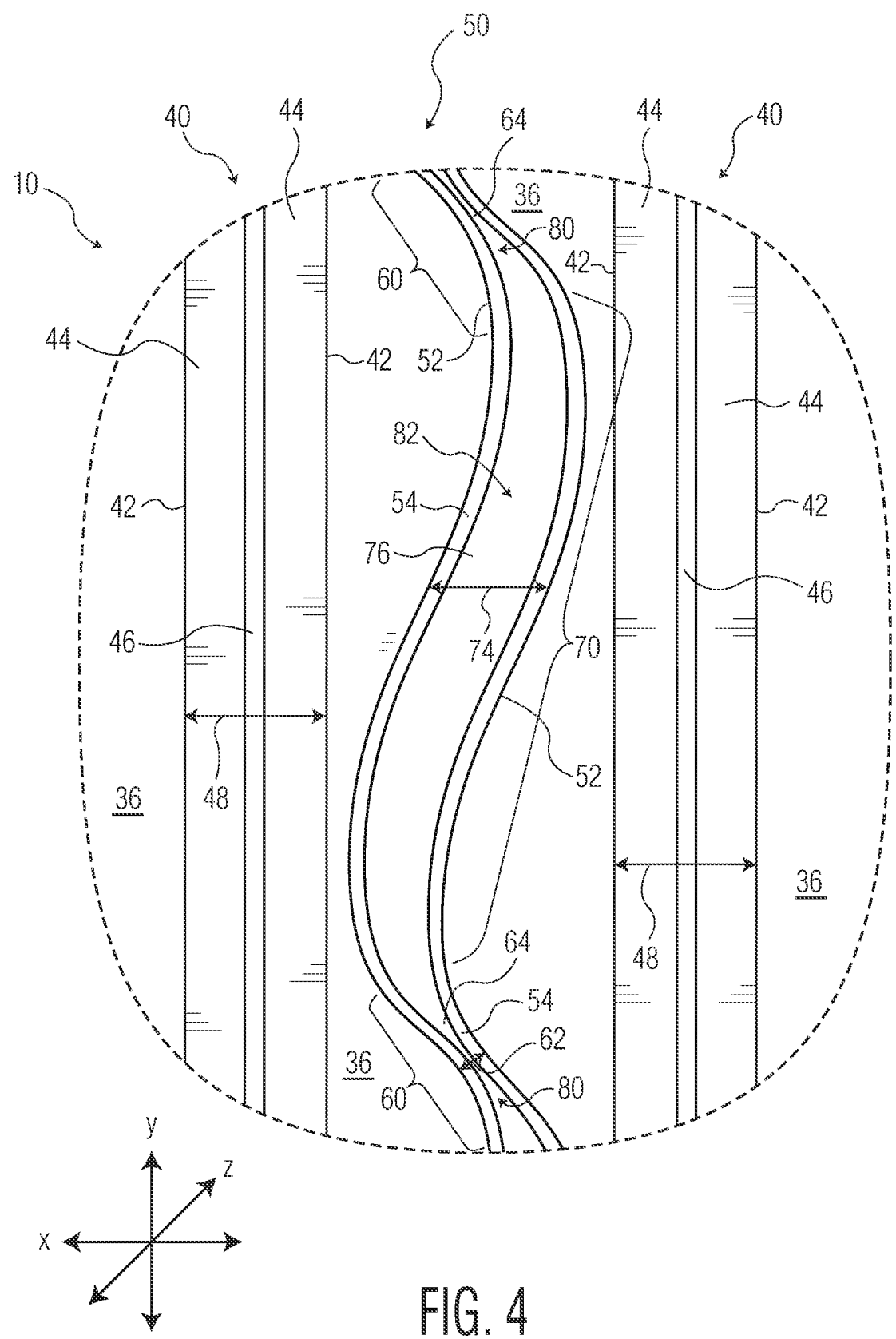
FIG. 4 is a close-up view of a portion of the tampon of FIG. 1.

In such embodiments in which the non-linear channel 50 can undulate in both the circumferential direction (X) as well as the radial depth direction (Z), the non-linear channel 50 can have multiple regions which have differing characteristics from each other. In various embodiments, a region of such a non-linear channel 50 may include a crest 80 and a uniform width between channel surface edges 52, or may include a crest 80 and a variable width between channel surface edges 52, or may include a trough 82 and a uniform width between channel surface edges 52, or may include a trough 82 and a variable width between channel surface edges 52. Such regions can be present in the non-linear channel 50 while the channel also undulates in the circumferential direction (X) as it extends in at least a portion of the longitudinal direction (Y) of the tampon 10. For example, as illustrated in FIGS. 1A-1C, 4 and 6, as a non-linear channel 50 extends in at least a portion of the longitudinal direction (Y) of the tampon 10, the non-linear channel 50 can undulate in the circumferential direction (X) and can have a variable depth dimension below the outer surface 36 of the tampon 10 wherein a first portion 64 of the inner surface defines a crest 80 in the radial depth direction (Z) and a second portion 76 of the inner surface defines a trough 82 in the radial depth direction (Z). The crest 80 can have a first depth dimension 84 below the outer surface 36 of the tampon 10 and the trough 82 can have a second depth dimension 86 below the outer surface 36 of the tampon 10 wherein the first depth dimension 36 and the second depth dimension 38 are not the same. In various embodiments, the first depth dimension 84 of a crest 80, as measured at the midpoint of the crest 80, of the non-linear channel 50 is from about 0.25, 0.3, 0.35 or 0.4 mm to about 0.45, 0.5, 0.55, 0.6, 0.65, 0.7, or 0.75 mm. In various embodiments, the second depth dimension 86 of a trough 82, as measured at the midpoint of the trough 82, of the non-linear channel 50 is from about 0.8, 0.85, 0.9, 0.95, or 1.0 mm to about 1.05, 1.1, 1.15, 1.2, 1.25, 1.3, or 1.35 mm. In various embodiments, the troughs 82 of the non-linear channel 50 can be separated from each other by a distance 88 of less than about 8, 7.6, 7, 6.6, 6, 5.6, or 5 mm. As further illustrated in the exemplary figures, the non-linear channel 50 can have a variable width between the channel surface edges 52, as measured at the outer surface 26 of the tampon 10, as the non-linear channel undulates in the circumferential direction (X). For example, as illustrated in the figures, the non-linear channel 50 can have a first region 60 wherein a first width 62 between the channel surface edges 52, as measured at the outer surface 36 of the tampon 10, is from about 0.35, 0.4, 0.45, 0.5, 0.55, 0.6, 0.65, 0.7, 0.75, or 0.8, mm to about 0.85, 0.9, 0.95, 1, 1.05, 1.1, 1.15, 1.2, 1.25, 1.3, 1.35, 1.4, 1.5, 1.75, 2.0, 2.5, 3.0, 3.5, 4.0, 5.0, or 6.0 mm and the non-linear channel 50 can have a second region 70 with a second width 74 between the channel surface edges 52, as measured at the outer surface 36 of the tampon 10, from about 0.35, 0.4, 0.45, 0.5, 0.55, 0.6, 0.65, 0.7, 0.75, or 0.8, mm to about 0.85, 0.9, 0.95, 1, 1.05, 1.1, 1.15, 1.2, 1.25, 1.3, 1.35, 1.4, 1.5, 1.75, 2.0, 2.5, 3.0, 3.5, 4.0, 5.0, or 6.0 mm wherein the first width 62 and the second width 74 are not the same. In various embodiments, a first width 62 of a first region 60 is not the same as a second width 74 of a second region 70. In various embodiments, a region, such as the second region 70, can also have a variable width within that region such as illustrated in FIG. 4.

In various embodiments, the first region 60 has a uniform width 62, as measured between the channel surface edges 52, and corresponds with a crest 80 which has a first depth 84 below the outer surface 36 of the tampon 10. In such embodiments, the second region 70 has a variable second width 74 within the second region 70 and the second width 70 is not the same as the first width 62 of the first region 60. The second region 70 also corresponds with a trough 82 which has a second depth 86 below the outer surface 36 of the tampon 10. In such embodiments, the non-linear channel 50 undulates in each of the circumferential direction (X) and the radial depth direction (Z) as the non-linear channel 50 extends in at least a portion of the longitudinal direction (Y) of the tampon 10.

In various embodiments, a tampon 10 can have at least 2, 3, 4, 5, 6, 7, 8, 9, or 10 linear channels 40 and at least 2, 3, 4, 5, 6, 7, 8, 9, or 10 non-linear channels 50. In various embodiments, a tampon 10 can have the same number of linear channels 40 and non-linear channels 50. In various embodiments, a tampon 10 can have 4 linear channels 40 and 4 non-linear channels 50. In various embodiments, a tampon 10 can have 6 linear channels 40 and 6 non-linear channels 50. In various embodiments, a tampon 10 can have 8 linear channels 40 and 8 non-linear channels 50. In various embodiments, a tampon 10 can have 10 linear channels 40 and 10 non-linear channels 50. In various embodiments, the number of linear channels 40 can differ from the number of non-linear channels 50. In various embodiments, the linear channel(s) 40 and the non-linear channel(s) 50 are present in an alternating pattern on the tampon 10. A linear channel 40 can be positioned between two non-linear channels 50 and a non-linear channel 50 can be positioned between two linear channels 40. In various embodiments, the non-linear channels 50 are congruent with each other such that the circumferential direction (X) undulation pattern of one non-linear channel 50 resembles the circumferential direction (X) undulation pattern of another non-linear channel 50. Two non-linear channels 50 can be considered congruent with each other when their circumferential direction (X) undulation patterns resemble each other, however, such resemblance does not require the width between the sidewalls 54 of a first non-linear channel 50 to be identical to the width between the sidewalls 54 of a second non-linear channel 50. Congruency between non-linear channels 50 is determined by viewing the undulation pattern (i.e., the back-and-forth pattern) in the circumferential direction (X).

In various embodiments, such as embodiments in which a non-linear channel 50 does not extend the total length 24 of the tampon 10, additional topographical elements can be provided on the tampon 10 wherein the additional topographical elements can be raised from the outer surface 36 and/or depressed into the outer surface 36 of the tampon 10. For example, the tampon 10 can have discrete indentations, discrete raised surfaces, and/or a circumferential raised ring in the portions of the tampon 10 wherein a non-linear channel 50 is not located.

In various embodiments, the tampon 30 can be placed into an applicator. In various embodiments, the tampon 30 may also include one or more additional features. For example, the tampon 30 may include a "protection" feature as exemplified by U.S. Pat. No. 6,840,927 to Hasse; U.S. 2004/0019317 to Takagi; U.S. Pat. No. 2,123,750 to Schulz, and the like. In various embodiments, the tampon 30 can include an "anatomical" shape as exemplified by U.S. Pat. No. 5,370,633 to Villata, an "expansion" feature as exemplified by U.S. Pat. No. 7,387,622 to Pauley, an "acquisition" feature as exemplified by U.S. 2005/0256484 to Chase; an "insertion" feature as exemplified by U.S. Pat. No. 2,112,021 to Harris, a "placement" feature as exemplified by U.S. Pat. No. 3,037,506 to Penska, or a "removal" feature as exemplified by U.S. Pat. No. 6,142,984 to Brown.

Figure 7:
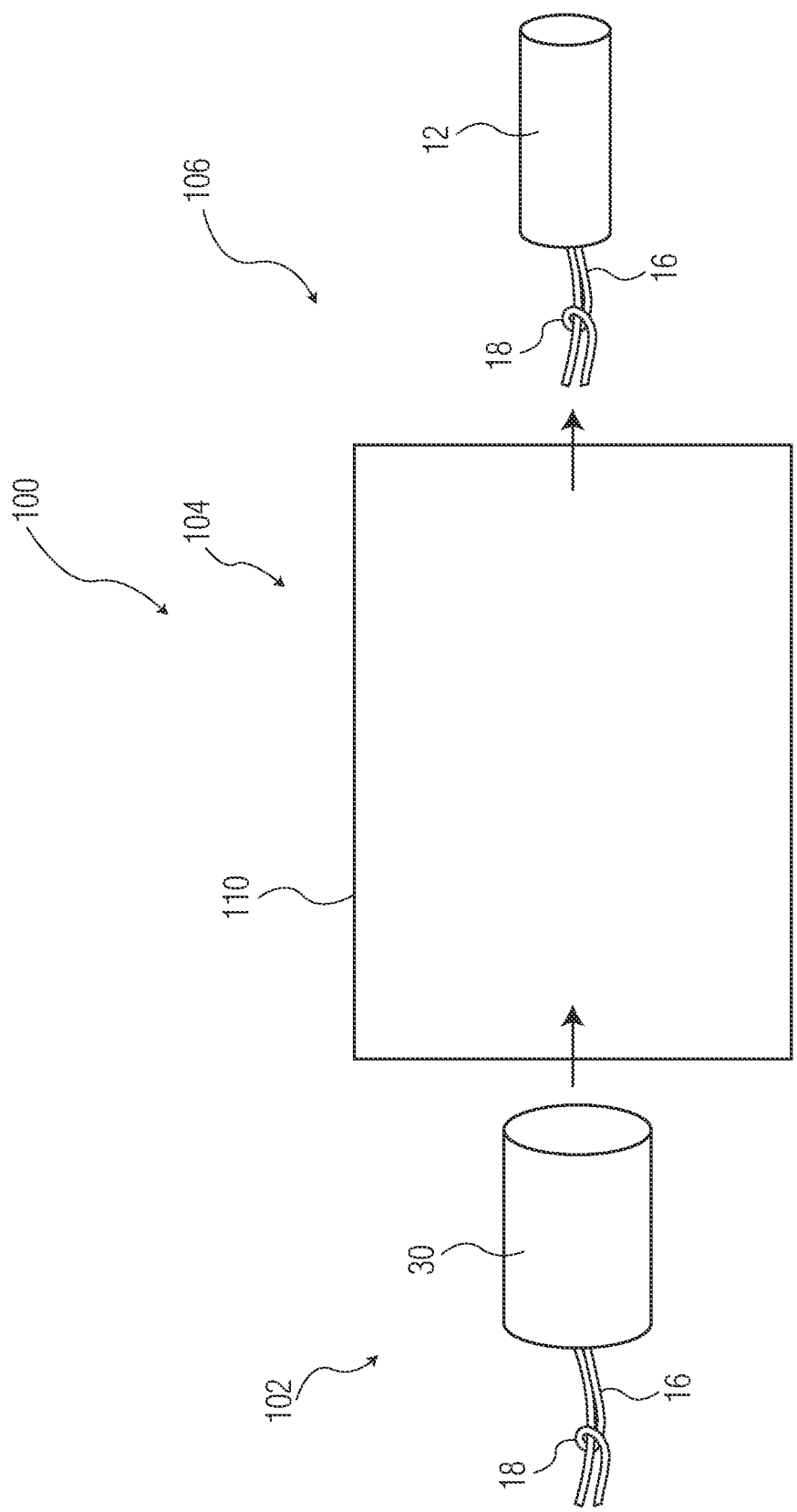
FIG. 7 is a schematic illustration of an exemplary embodiment of a method for compressing a tampon blank.
Figure 8:
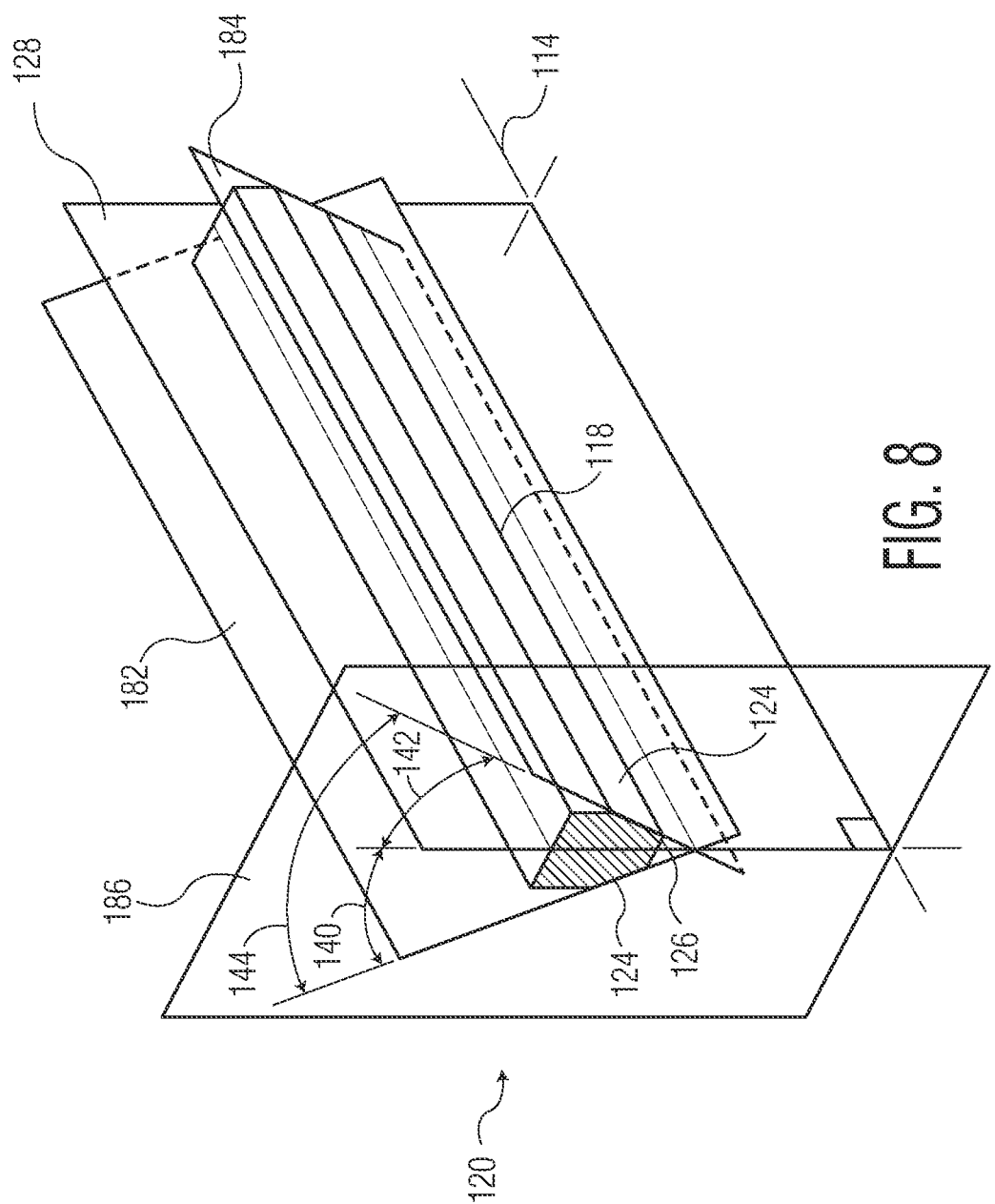
FIG. 8 is a perspective view of an illustration of an exemplary embodiment of a compression jaw.

Method and Apparatus:

A tampon blank 30 can undergo a compression step during the manufacturing process to form the pledget 12 of a tampon 10. Referring to FIG. 7, a schematic illustration of an exemplary method 100 for compressing a tampon blank 30 in the manufacture of a pledget 12 for a tampon 10 is illustrated. The method 100 includes a step 102 of providing a tampon blank 30 to a compression apparatus 110. The tampon blank 30 can be as described herein and has an initial diameter before being inserted into the compression space 112 of the compression apparatus 110. To compress the tampon blank 30 into the pledget 12 the compression apparatus 110 has a set of compression jaws 120 and a set of penetration jaws 130. In various embodiments, the compression apparatus 110 has at least 2, 3, 4, 5, 6, 7, 8, 9, or 10 compression jaws 120. In various embodiments, the compression jaws 120 are heated. In various embodiments, the compression apparatus 110 has at least 2, 3, 4, 5, 6, 7, 8, 9, or 10 penetration jaws 130. In various embodiments, the penetration jaws 130 are heated.

Referring to FIGS. 8, 8A-8L, a compression jaw 120 can have a compression segment 122. The compression segment 122 is that portion of the compression jaw 120 which initiates compression of the tampon blank 30 and which becomes surrounded by the absorbent material 14 of the tampon blank 30 during compression of the tampon blank 30. The compression segment 122 can have an opposing pair of sidewalls 124 which join together to form a compression surface 126. Each of the opposing pair of sidewalls 124 extend in the longitudinal direction of the compression space 112 of the compression apparatus so as to form a channel, such as linear channel 40, in the longitudinal direction (Y) of a pledget 12 during the compression of the tampon blank 30. The compression segment 122 can have any shape as desired to produce the desired shape and configuration of the linear channel 40. For example, in various embodiments, a linear channel 40 having a shape and configuration such as illustrated in FIG. 5A may be deemed suitable for the pledget 12, and resultant tampon 10, and a compression segment 122 can have the shape and configuration illustrated in FIG. 8A. For example, in various embodiments, a linear channel 40 having a shape and configuration such as illustrated in FIGS. 5B-5L may be deemed suitable for the pledget 12, and resultant tampon 10, and a compression segment 122 can have the shape and configuration such as illustrated in FIGS. 8B-8L, respectively, (i.e., the compression segment 122 of FIG. 8B can produce the channel of FIG. 5B, the compression segment 122 of FIG. 8C can produce the channel of FIG. 5C, the compression segment 122 of FIG. 8D can produce the channel of FIG. 5D, the compression segment 122 of FIG. 8E can produce the channel of FIG. 5E, the compression segment 122 of FIG. 8F can produce the channel of FIG. 5F, the compression segment 122 of FIG. 8G can produce the channel of FIG. 5G, the compression segment 122 of FIG. 8H can produce the channel of FIG. 5H, the compression segment 122 of FIG. 8I can produce the channel of FIG. 5I, the compression segment 122 of FIG. 8J can produce the channel of FIG. 5J, the compression segment 122 of FIG. 8K can produce the channel of FIG. 5K, and the compression segment 122 of FIG. 8L can produce the channel of FIG. 5L.

The plurality of compression segments 122 of the respective compression jaws 120 guide the concentric positioning of the tampon blank 30 into the compression space 112 of the compression apparatus 110. As the compression segments 122 will guide the tampon blank 30 into the compression space 112, the compression segments 122 should not inhibit the movement of the tampon blank 30 into the compression space 112 of the compression apparatus 110 and the compression segments 122 can be designed to have a shape and configuration that can reduce friction between the tampon blank 30 and the compression segments 122.

The plurality of compression segments 122 of the respective compression jaws 120 are also used to guide the concentric positioning of the pledget 12 out of the compression apparatus 110 during the step of ejecting the pledget 12 from the compression apparatus 110. As the compression segment 122 will guide the pledget 12 during ejection of the pledget 12 from the compression apparatus 110, the compression segment 122 should not inhibit the movement of the pledget 12 from the compression apparatus 110. As such, the compression segment 122 can be designed to have a shape and configuration that can reduce friction between the pledget 12 and the compression segment 122.

During both insertion of a tampon blank 30 into the compression space 112 and ejection of the pledget 12 from the compression space 112, therefore, the compression segments 122 of the compression jaws 120 are in contact with the tampon blank 30 or pledget 12, respectively, to provide for concentric positioning relative to the longitudinal axis 114 of the compression apparatus 110.

Referring to FIGS. 8, 8A-8L, to reduce the friction between the tampon blank 30 or pledget 12 and the compression segment 122, the compression segment 122 can be designed such that at least one of the sidewalls 124 is oblique to a radial plane 128 directed outwards from the longitudinal axis 114 of the compression space 112 of the compression apparatus 110. A radial plane 128 extends outward from the longitudinal axis 114 and contains the longitudinal axis 114 of the compression space 112 of the compression apparatus 110. A compression surface 126 has two compression edges 118 that are parallel with the longitudinal axis 114 of the compression apparatus 110. The two sidewalls 124 join together with the compression surface 126 at a corresponding compression edge 118 to form the compression segment 122 of compression jaw 120 to form a correspondingly shaped linear channel 40.

The compression surface 126 can be any suitable width and contour to form the desired shaped inner surface 46 that defines the bottom of the linear channel 40. Referring to FIGS. 5B, 5C, 5G, 5K, and 5L the linear channel 40 contour of the inner surface 46 is formed by an arcuate shaped compression surface 126, and in FIGS. 5D, 5E, 5F, 5I, and 5J, the linear channel 40 contour of the inner surface 46 is formed by a flat compression surface 126.

The compression edges 118 of the compression surface 126 can either be coincident with one another to form a compression surface 126 such as in the channel shape of FIGS. 5A and 5H, or the compression edges 118 can be separated any suitable distance from one another to form a flat, arcuate, or contoured compression surface 126 to form a corresponding inner surface 46 of the linear channel 40.

Sidewalls 124 can be of any suitable contour including as flat or arcuate to form a correspondingly shaped linear channel 40 sidewall 44. Each compression segment 122 of the compression jaw 120 has a pair of sidewalls 124 that have an engagement surface (i.e., that portion of the sidewall 124 which will contact the tampon blank 30), at least a portion of which defines a sidewall plane. A sidewall plane is tangent to the respective sidewall 124 surface and contains the corresponding compression edge 118 of the compression surface 126 that contacts the respective sidewall 124. A lateral cross-section plane is orthogonal to the longitudinal axis 114 of the compression space 112 and contains an acute angle 140 defined between the radial plan 128 and a first sidewall plane 182, and an acute angle 142 defined between the radial plane 128 and a second sidewall plane 184, and a corresponding total angle 144 is defined between the first sidewall plane 182 and the second sidewall plane 184.

At least one of the sidewalls 124 of the compression segment 122 is oblique to the radial plane 128 directed outward from the longitudinal axis of the compression space 122. Referring to FIGS. 8 and 8A-8L, the compression segment 122 has a first sidewall 124 having an acute angle 140 from the radial plane 128 from about 0, 5, 10, 15, 35, or 40 degrees to about 45, 50, 55, 60, 65, 70, 80, or 89 degrees and the second sidewall 124 has an acute angle 142 from the radial plane from about 0, 5, 10, 15, 35, or 40 degrees to about 45, 50, 55, 60, 65, 70, 80, or 89 degrees. A total angle 144 between the two opposing sidewall planes, 182 and 184, of sidewalls 124 can be from about 10, 20, 30, 35 or 40 to about 45, 60, 70, 80, 90, 120, 150, or 178 degrees.

Figure 9B:
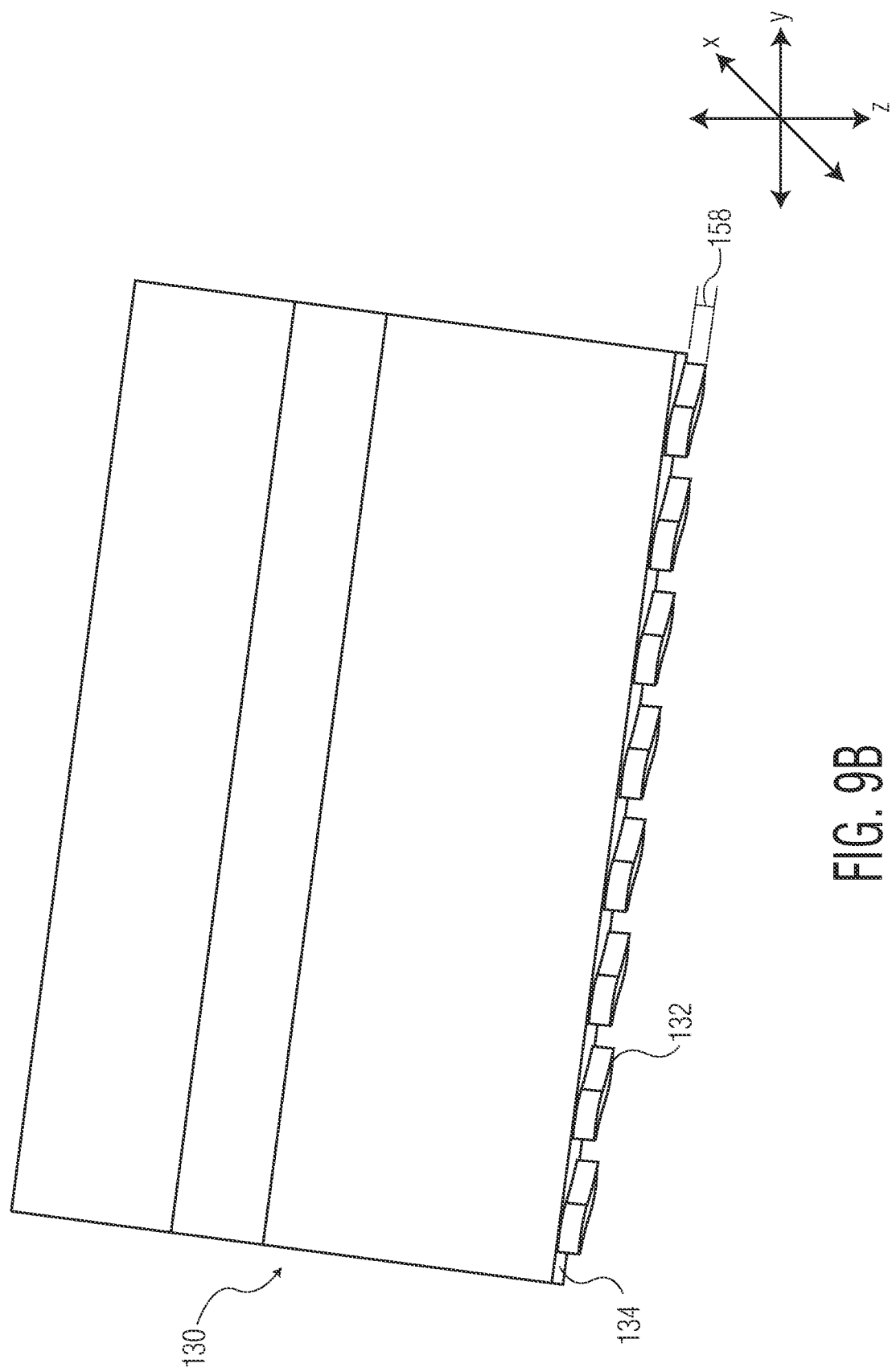
FIG. 9B is a bottom view of the penetration jaw of FIG. 9A.
Figure 9C:
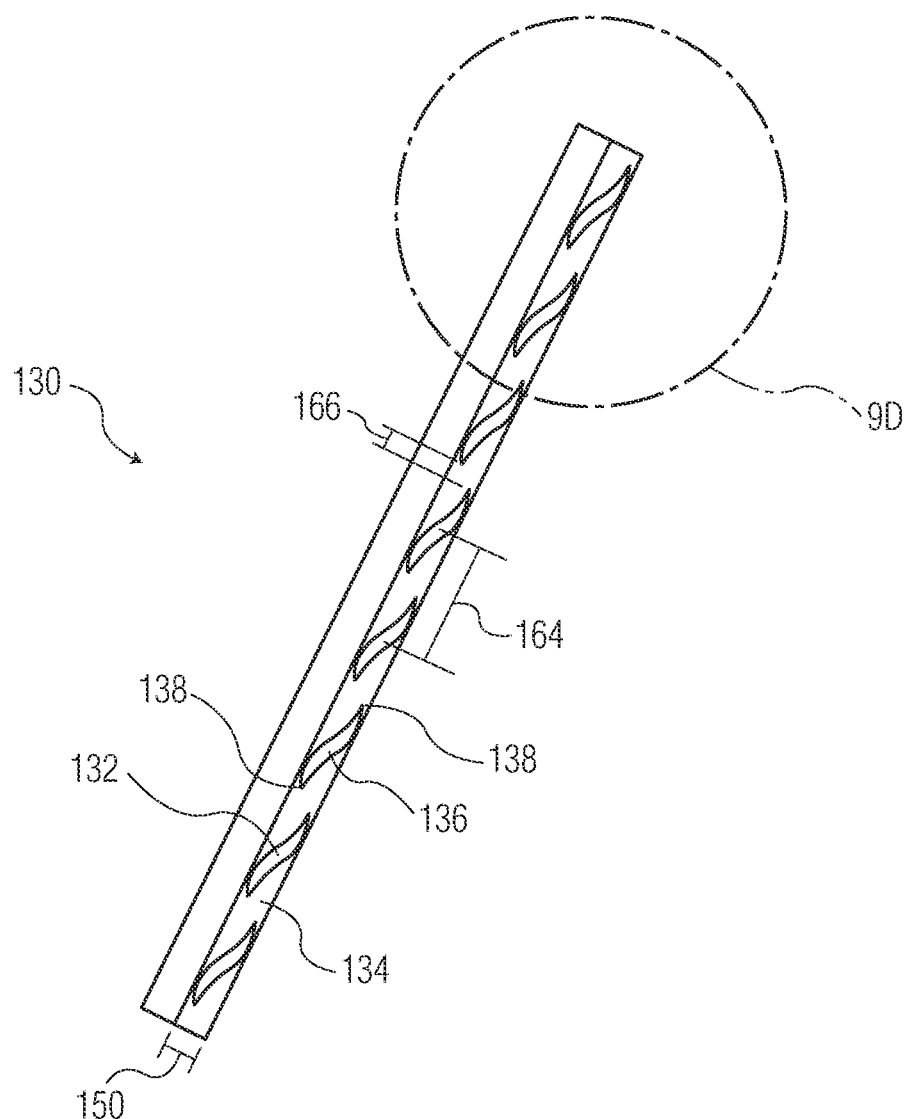
FIG. 9C a side view of the penetration jaw of FIG. 9A.
Figure 9D:
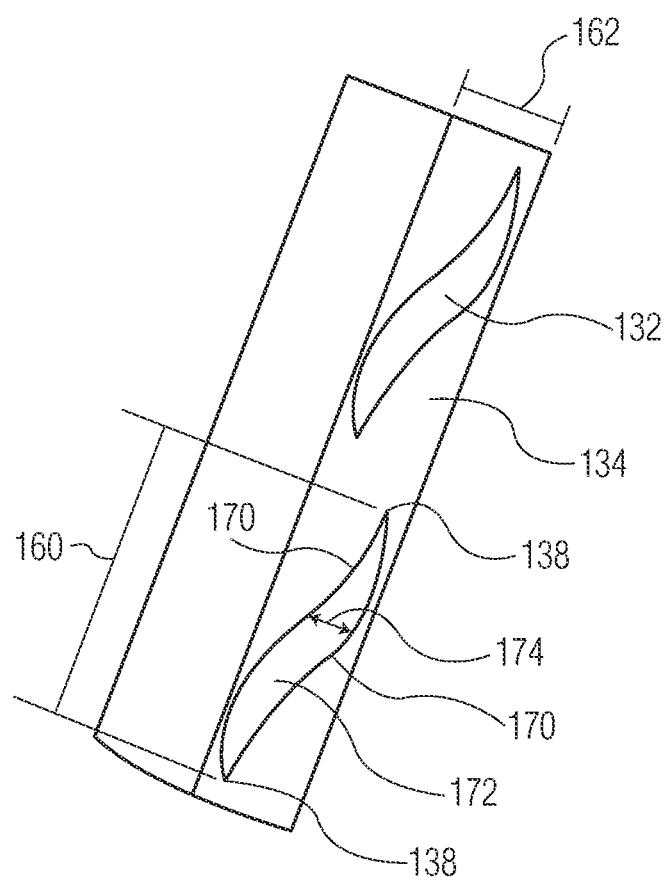
FIG. 9D is a close-up view of a portion of the penetration jaw of FIG. 9C.

To form a non-linear channel, such as non-linear channel 50, into the tampon blank 30, the compression apparatus can have penetration jaws 130. A penetration jaw 130 can have a base surface 134 with multiple penetration segments 132 extending outwardly from the base surface 134. The penetration segments 132 can be of any shape, size, or configuration as deemed suitable. In various embodiments, the penetration jaw 130 can have at least 4, 5, 6, 7, 8, 9, 10, 11, 12, 13, 14, 15, 20, 30, or 35 penetration segments 132 extending from the base surface 134. Referring to FIGS. 9A-9D, an exemplary embodiment of a penetration jaw 130 is illustrated. FIG. 9A illustrates a perspective view of a penetration jaw 130, FIG. 9B is a bottom view of the penetration jaw 130 of FIG. 9A, FIG. 9C is a side view of the penetration jaw 130 of FIG. 9A so the penetration surfaces 172 of the penetration segments 132 are visible to the viewer, and FIG. 9D is a close-up of a portion of the penetration jaw 130 of FIG. 9C. In various embodiments, the penetration jaw 130 can have a longitudinal direction (Y) such that it extends in the longitudinal direction of the compression space 112 of the compression apparatus 110.

The penetration jaw 130 further has a lateral direction (X). The base surface 134 can have a width dimension 150, as measured in the lateral direction (X), from about 1.6 or 1.7 mm to about 1.8, 1.9, 2.0, 2.2, 2.4, 2.6, 2.8, 3.0, 3.5, 4.0, 4.5, 5.0, 5.5, or 6.0 mm. The penetration segments 132 can extend from the base surface 134 of the penetration jaw 130 any distance 158 as deemed suitable such that the penetration segments can penetrate into the tampon blank 30 during compression of the tampon blank 30. In various embodiments, the penetration segments 132 can extend a distance 158 from the base surface, as measured from the base surface 134 to the outermost point of the penetration segment 132, of from about 0.6, 0.8, 1.0, 1.2, 1.4, 1.45, 1.5, 1.55, 1.6, or 1.65 mm to about 1.7, 1.75, 1.8, 1.85, 1.9, 1.95, 2.05, 2.25, 2.45, 2.55, 2.65, or 2.75 mm.

Figure 10:
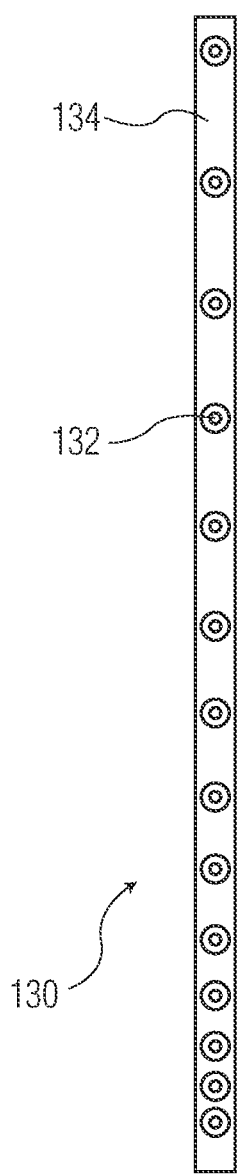
FIG. 10 is a side view of an exemplary embodiment of a penetration jaw.
Figure 10A:
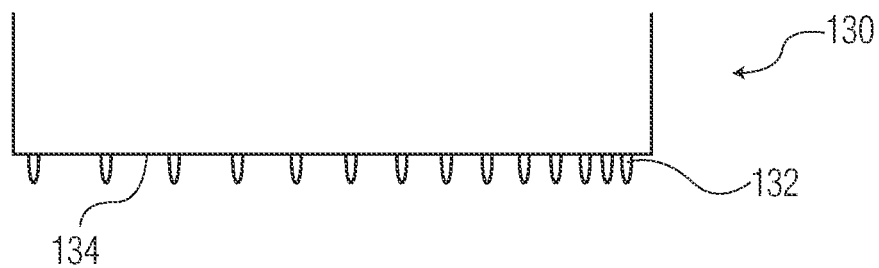
FIG. 10A is a bottom view of the penetration jaw of FIG. 10.

As the penetration jaw 130 can have multiple penetration segments 132 extending outwardly from the base surface 134, the penetration segments 132 can be in a spaced apart relationship from each other. In various embodiments, the distance 166 from one penetration segment 132 to the next successive penetration segment can be from about 0.2, 0.4, 0.6, 0.8, 1, 1.2, 1.4, 1.6, 1.8, 2, 2.6, 3, 3.6, or 4 mm to about 4.6, 5, 5.6, 6, 6.6, 7, 7.6, or 8 mm. In various embodiments, the penetration segments 132 can be evenly spaced apart from each other, such as illustrated in FIGS. 9A-9D. In various embodiments, the penetration segments 132 can vary in their spacing, such as illustrated in FIGS. 10 and 10A. FIG. 10 provides a side view of an exemplary embodiment of a penetration jaw 130 with multiple penetration segments 132 extending outwardly from the base surface 134 and FIG. 10A provides a bottom view of the penetration jaw 130 of FIG. 10. As illustrated in FIGS. 10 and 10A, the penetration segments 132 are in the shape of concentric cones and are spaced apart from each other in a variable distance.

A penetration segment 132 can have a length dimension 160 and a widest width dimension 162. The length dimension 160 can be measured in the longitudinal direction (Y) of the penetration jaw 130 and the widest width dimension 162 can be measured in the lateral direction (X) of the penetration jaw 130. In various embodiments, the length dimension 160 of the penetration segment 132 can be from about 1.5, 1.6, 1.7, 1.8, 1.9, 2, 2.2, 2.4, 2.6, 2.8, 3, 3.2, 3.4, 3.6, 3.8, or 4 mm to about 4.2, 4.4, 4.6, 4.8, 5, 5.2, 5.4, 5.6, 5.8, 6, 6.2, 6.4, 6.6, 6.8, 7, 7.2, 7.4, 7.6, 7.8 or 8 mm. For example, the length dimension 160 of the penetration segment 132 illustrated in FIG. 9D can be measured between the opposing tips 138 of the penetration segment 132. In various embodiments, the penetration segment 132 can have a widest width dimension 162. Such a widest width dimension 162 can be measured at the widest width of the penetration segment 132 in the lateral direction (X) of the penetration jaw 130. In various embodiments, the widest width dimension 162 of the penetration segment can be from about 1, 1.2, or 1.4 mm to about 1.6, 1.7, 1.8, 2.0, 2.2, 2.4, 2.6, 2.8, 3.0, 3.5, 4.0, 4.5, 5.0, 5.5, or 6.0 mm.

The penetration segment 132 has a pair of opposing sidewalls 170 which extend away from the base surface 134 and join together to form a penetration surface 172. In various embodiments, the penetration segment 132 can be provided in a variety of shapes and configurations. In various embodiments, the penetration segment 132 can be provided in shapes such as an oval, cone, triangle, diamond, circle, or tilde. In various embodiments, a penetration segment 132 can have a variable width dimension 174 between the opposing pair of sidewalls 170 in the lateral direction (X) as the penetration segment 132 extends in the longitudinal direction (Y) of the penetration jaw 130. The variable width dimension 174 of the penetration segment 132 is, therefore, a measurement between the sidewalls 170 of the penetration segment 132 while the widest width dimension 162 is a measurement of the overall width of the penetration segment 132 in the lateral direction (X) of the penetration jaw 130. For example, as illustrated in FIGS. 9A-9D, the penetration segment 132 is in the shape of a tilde. As illustrated, the widest width dimension 162 of the penetration segment 132 is substantially similar to the full width dimension 150 of the base surface 134, however, the actual penetration segment 132, as a tilde, has a variable width dimension 174 between the opposing sidewalls 170 in the lateral direction (X) as the tilde extends in the longitudinal direction (Y) of the penetration jaw 130. In various embodiments, the variable width dimension 174 of the penetration segment 132 can be from about 0.3, 0.35, 0.4, 0.45, 0.5, 0.55 or 0.6 mm to about 0.65, 0.7, 0.75, 0.8, 0.85, 0.9, 0.95, 1, 1.05, 1.1, 1.15, 1.2, 1.25, 1.3, 1.35, or 1.4 mm.

Figure 11:
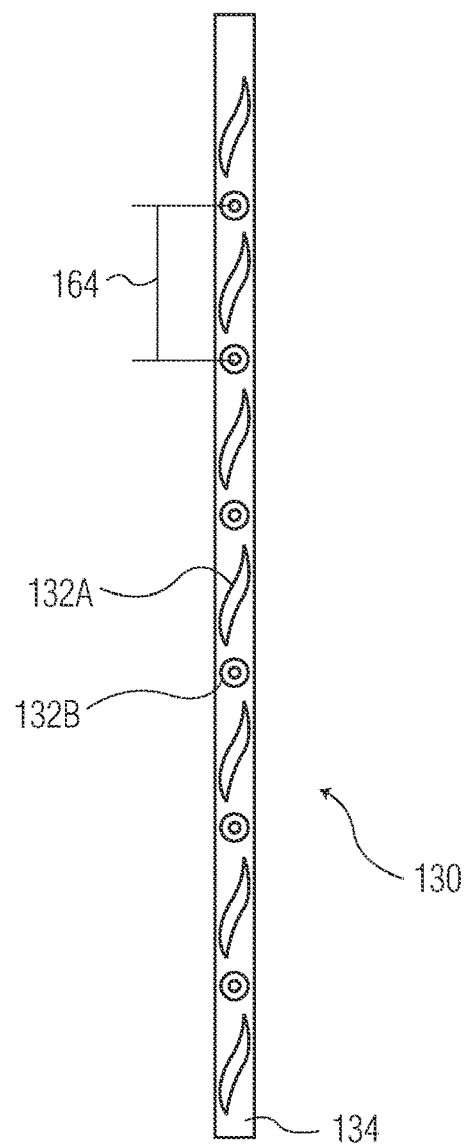
FIG. 11 is a side view of an exemplary embodiment of a penetration jaw.
Figure 11A:
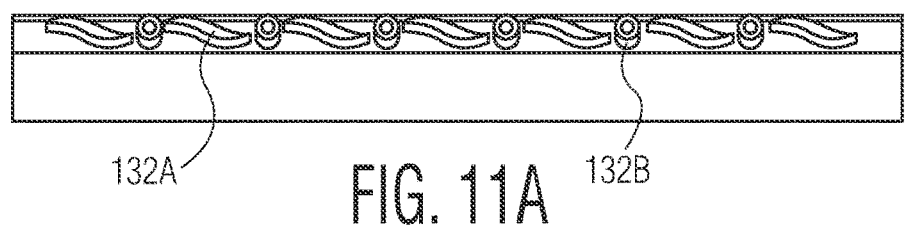
FIG. 11A is a perspective view of the penetration jaw of FIG. 11.
Figure 12:
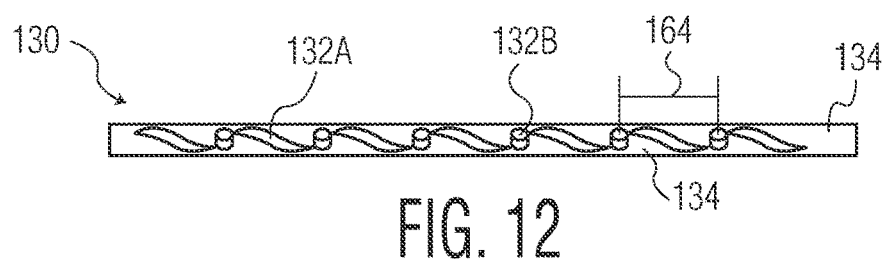
FIG. 12 is a side perspective view of an exemplary embodiment of a penetration jaw.

In various embodiments, the penetration segments 132 can be provided in a pattern of penetration segments 132. In various embodiments, the pattern can have a single style and configuration of penetration segment 132 such as illustrated in FIGS. 9A-9D. In various embodiments, the pattern can have at least two styles of penetration segments 132, such as penetration segments 132A and 132B illustrated in FIGS. 11, 11A, and 12. The pattern of penetration segments can be provided in a repeating pattern wherein a distance 164 from one pattern to the next pattern can be from about 2, 2.5, 3, 3.5, 4, 4.5, 5, 5.5, 6, 7, 7.5, or 8 mm to about 8.5, 9, 9.5, or 10 mm. As illustrated in FIGS. 11 and 11A, the pattern can be a repeating pattern of penetration segments, 132A and 132B, in the style of a tilde and concentric cone, respectively. As illustrated in FIG. 12, the pattern can be a repeating pattern of penetration segments, 132A and 132B, of a tilde and circular cylinder. In various embodiments, the penetration segments 132 on a penetration jaw can be of at least two different styles wherein each style is grouped together to provide for a tampon 10 having a non-linear channel 50 wherein different portions of the non-linear channel 50 are of different patterns. Referring to FIG. 13, a tampon 10 can have a non-linear channel 50 in which a first portion of a non-linear channel 50 is linked circles and a second portion of the non-linear channel 50 is a tilde pattern.

In various embodiments, the penetration segments 132 can extend in at least a portion of the longitudinal direction (Y) of the penetration jaw 130. In various embodiments, the penetration segments 132 can extend the total length of the penetration jaw 130 in the longitudinal direction (Y). In various embodiments, the penetration segments 132 can extend a portion of the total length of the penetration jaw 130 in the longitudinal direction (Y). For example, the penetration segments 132 can be positioned on the length of the penetration jaw 130 in the longitudinal direction (Y) such that the resulting tampon 10 can have a non-linear channel 50 which can extend from the insertion end 20 to approximately the middle of the tampon length 24 of the tampon 10. In various embodiments, the penetration segments 132 can be positioned on the length of the penetration jaw 130 in the longitudinal direction (Y) such that the resulting tampon 10 can have a non-linear channel 50 which extends only a portion of the tampon length 24 of the tampon 10 such as a non-linear channel 50 which extends from the insertion end 20 to the middle of the tampon length 24 of the tampon 10, from the withdrawal end 22 to the middle of the tampon length 24 of the tampon 10, or can be present in the middle third of the tampon 10 without extending to either of the insertion end 20 or withdrawal end 22. In various embodiments, the penetration segments 132 can be positioned on the length of the penetration jaw 130 in the longitudinal direction (Y) such that the resultant tampon 10 can have multiple non-linear channels 50 present in a common region of the tampon 10 such as, for example, a tampon 10 can have a first non-linear channel 50 in a spaced apart relationship in the longitudinal direction (Y) from a second non-linear channel 50. For example, a tampon 10 can have a first non-linear channel 50 present at the insertion end 20 and extending in the longitudinal direction (Y) towards the middle of the tampon length 24 of the tampon 10 and a second non-linear channel 50 present at the withdrawal end 22 of the tampon and extending towards the middle of the tampon length 24 of the tampon 10 wherein the first non-linear channel 50 and the second non-linear channel 50 are present in the same longitudinal plane of the tampon 10 and separated from each other by a distance in the longitudinal direction (Y).

An example of an embodiment of a penetration jaw 130 is illustrated in FIGS. 9A-9D. In the example illustrated in FIGS. 9A-9D, the penetration jaw 130 has a base surface 134 and eight penetration segments 132 in the shape of a tilde extending outwardly from the base surface 134 of the penetration jaw. Each penetration segment 132 extends outwardly from the base surface 134 at a distance 158 of about 1.85 mm. The base surface 134 has a width dimension 150 of about 2.5 mm and the penetration segments 132 have a widest width dimension 162 of about 1.8 mm. Each penetration segment 132 is evenly spaced from each successive penetration segment 132 at a distance 166 from about 0.2 mm to about 1.7 mm. The length dimension 160 of each penetration segment 132 can be from about 6.2 mm to about 7.8 mm. The penetration segments 132, in the shape of a tilde, can have a variable width 174 between the opposing sidewalls 170 which can be from about 0.3 mm to about 1.4 mm. The penetration segments 132 are provided on the penetration jaw 130 in a repeating pattern of the single style of penetration segments 132, the tilde.

An example of an additional embodiment of a penetration jaw 130 is illustrated in FIGS. 11 and 11A. In the example illustrated in FIGS. 11 and 11A, the penetration jaw 130 has a base surface 134 and thirteen penetration segments 132 extending outwardly from the base surface 134. Each penetration segment, 132A and 132B, extends outwardly from the base surface 134 at a distance of about 1.85 mm. The base surface 134 has a width dimension of about 2.5 mm and the penetration segment 132 have a widest width dimension 162 of about 1.8 mm. Each penetration segment, 132A or 132B, is evenly spaced from each successive penetration segment, 132A or 132B, at a distance of about 0.4 mm. The length dimension 160 of each penetration segment 132A is about 7 mm and the length dimension 160 of each penetration segment 132B is about 2 mm. The penetration segment 132A, in the shape of a tilde, can have a variable width between the opposing sidewalls 170 which can be from about 0.3 mm to about 1.4 mm. The penetration segments 132 are provided on the penetration jaw 130 in a repeating patter of two styles and shapes of penetrating segments wherein penetration segment 132A is in the shape of a tilde and penetration segment 132B is in the shape of a concentric circular ring.

Figure 14:
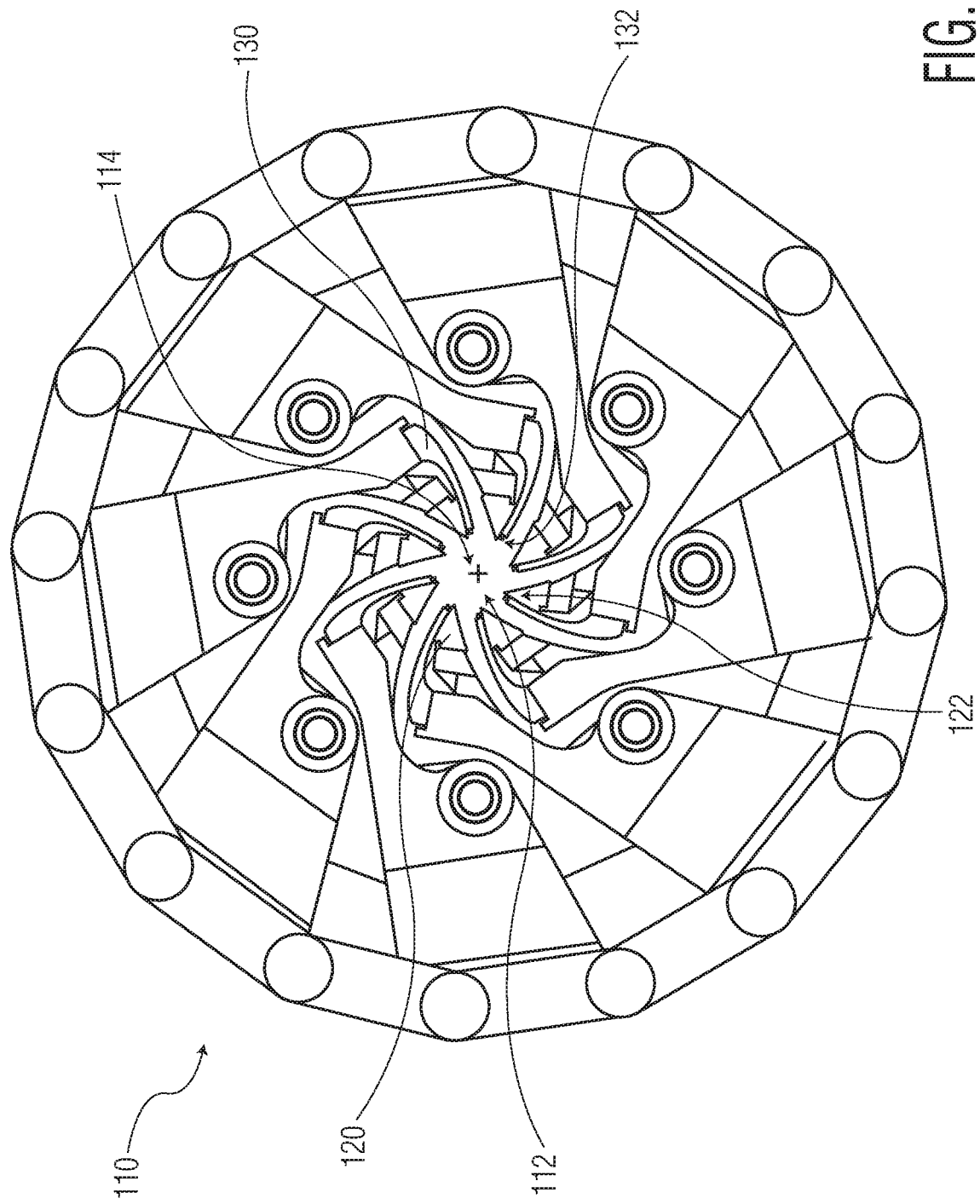
FIG. 14 is a schematic illustration of a compression apparatus wherein the compression jaws and the penetration jaws move in an arcuate path towards the longitudinal axis of the compression space of the compression apparatus and wherein the compression jaws and the penetration jaws are in an open configuration to receive an uncompressed tampon blank.
Figure 15:
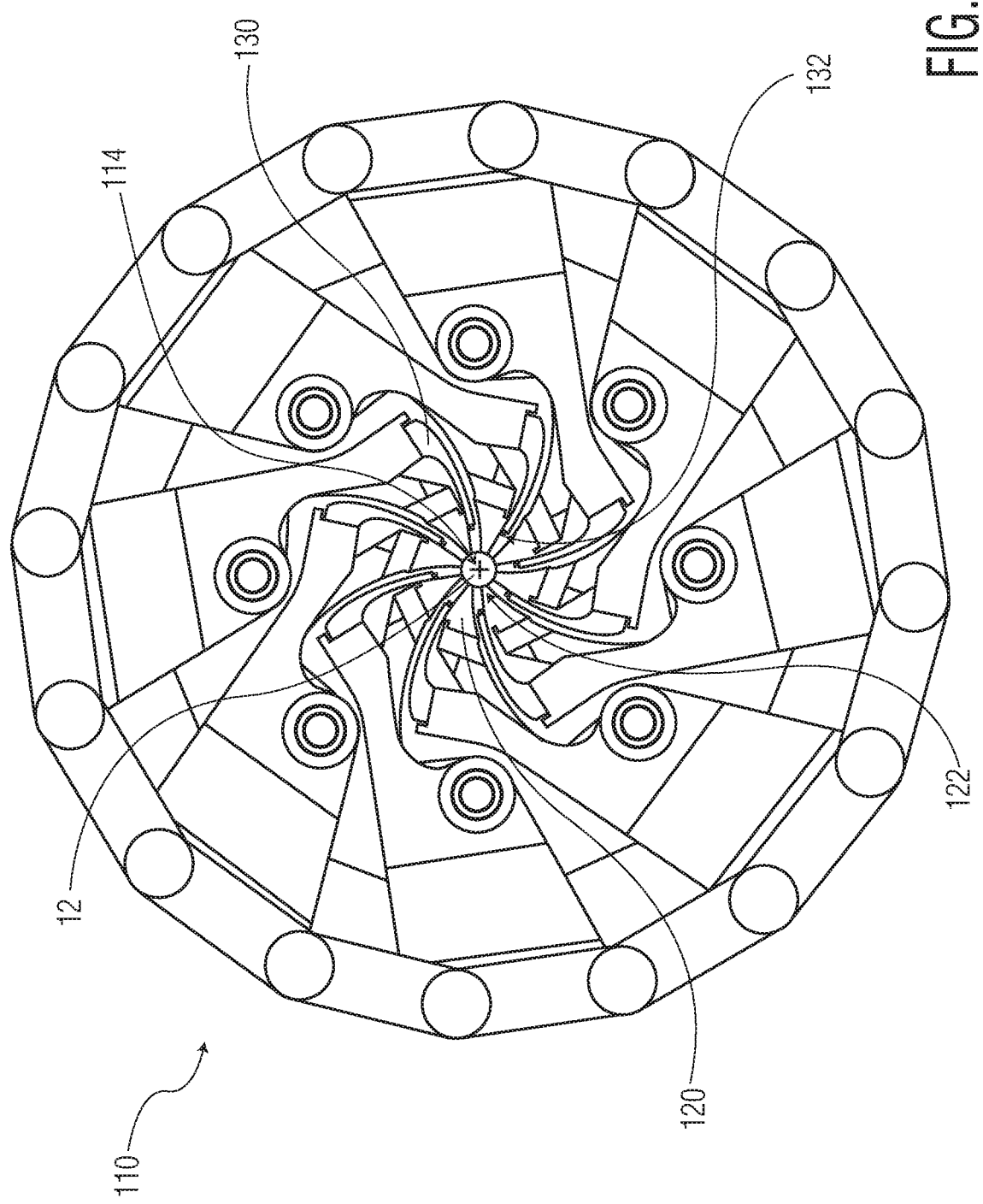
FIG. 15 is a schematic illustration of the compression apparatus of FIG. 14 with the compression jaws in a closed configuration and compressing a tampon blank to form a tampon pledget.
Figure 16:
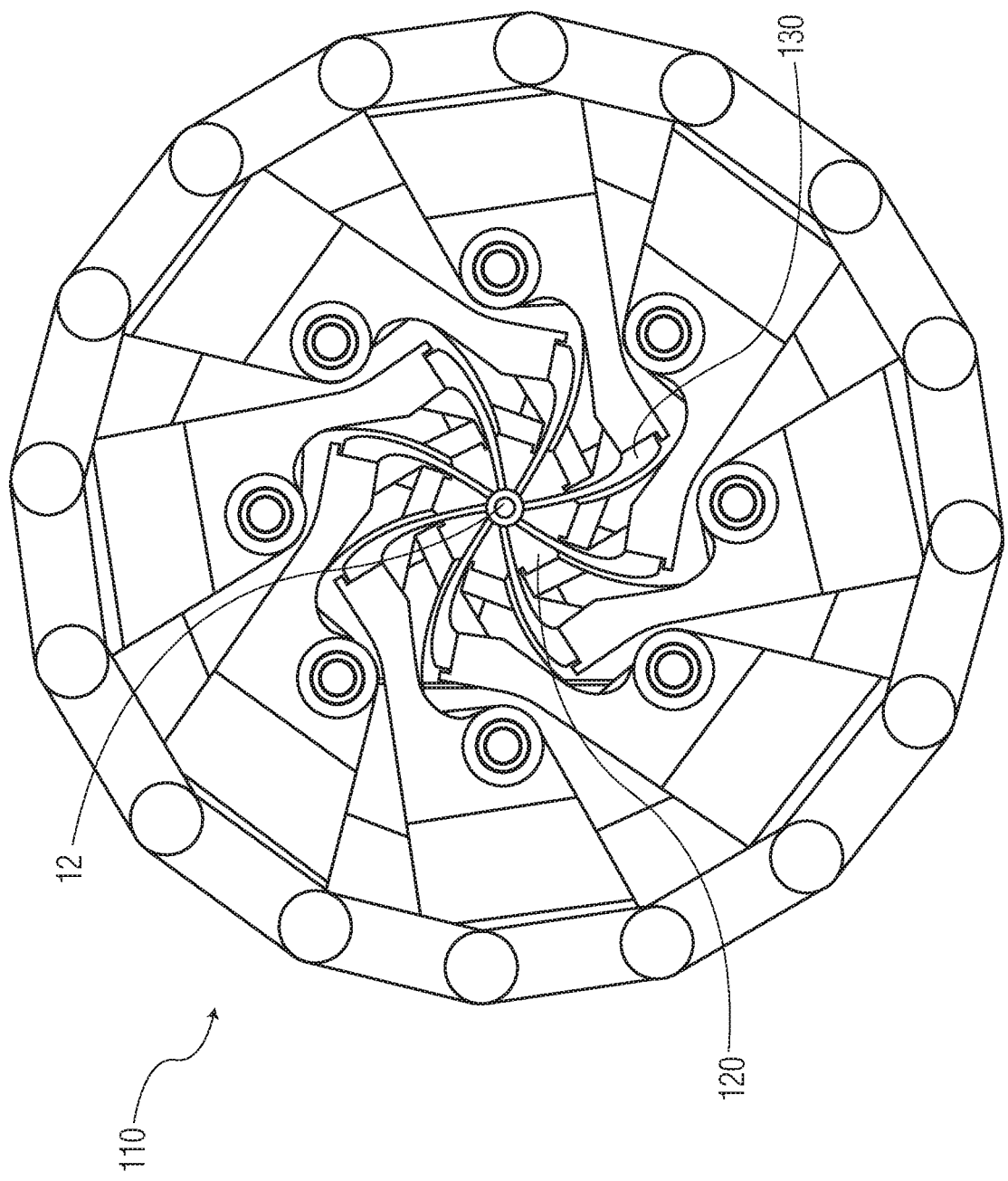
FIG. 16 is a schematic illustration of the compression apparatus of FIG. 14 with the compression jaws and penetration jaws in a closed configuration and compressing the tampon pledget.
Figure 17:
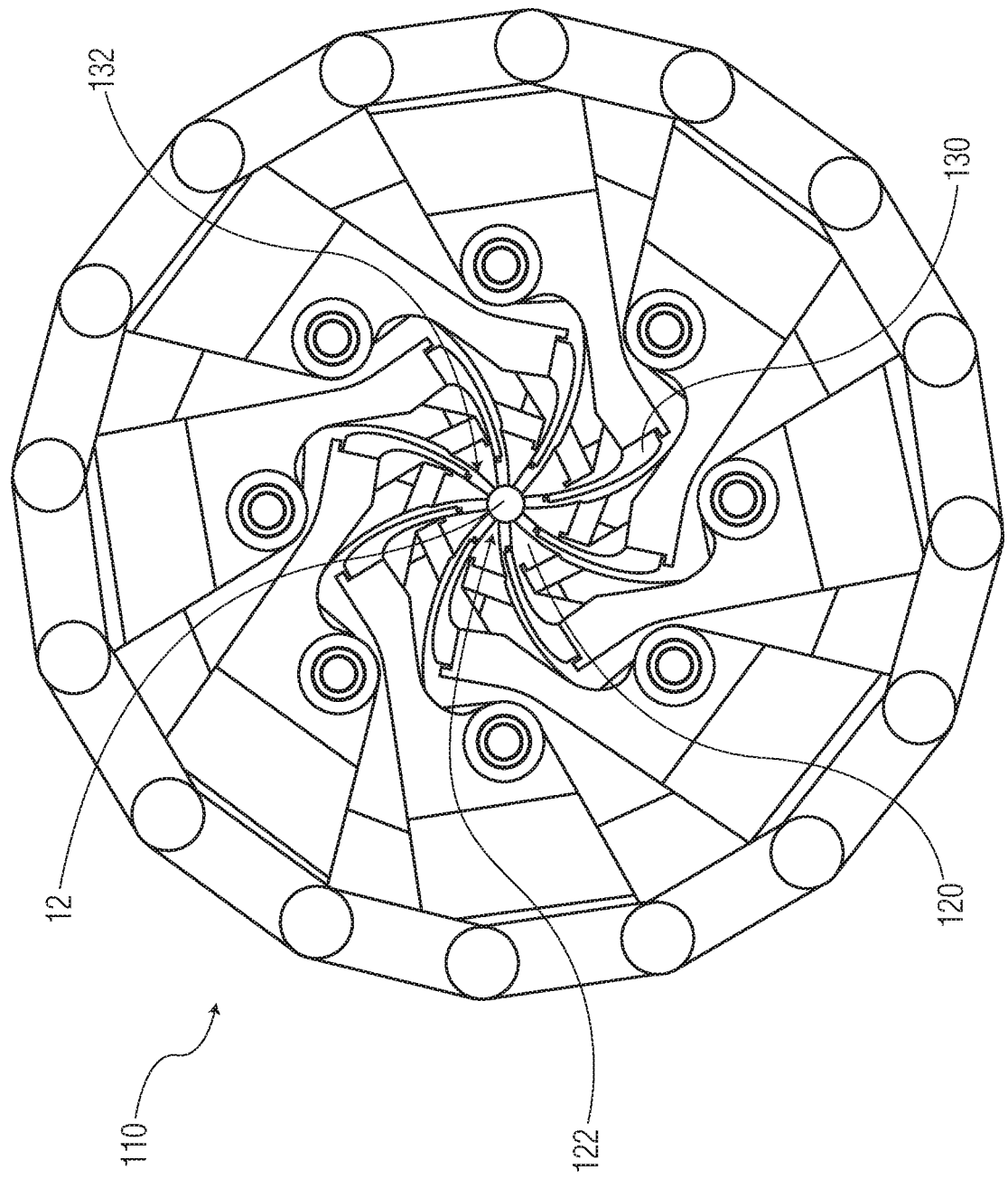
FIG. 17 is a schematic illustration of the compression apparatus of FIG. 14 with the penetration jaws in an open configuration and completely withdrawn from the tampon pledget and the compression jaws in a closed configuration.

In various embodiments, the compression jaws 120 and the penetration jaws 130 can be provided in a compression apparatus 110 wherein the compression apparatus 110 will open and close the compression jaws 120 and penetration jaws 130 in a radial direction along an arcuate path, such as a compression apparatus 110 illustrated in FIGS. 14-17. FIG. 14 is a schematic illustration of a compression apparatus wherein the compression jaws 120 and the penetration jaws 130 move in an arcuate path towards the longitudinal axis 114 of the compression space 112 of the compression apparatus 110 and wherein the compression jaws 120 and the penetration jaws 130 are in an open configuration. FIG. 15 is a schematic illustration of the compression apparatus 110 of FIG. 14 with the compression jaws 120 in a closed configuration and compressing a tampon blank 30 to form a tampon pledget 12. FIG. 16 is a schematic illustration of the compression apparatus 110 of FIG. 14 with the compression jaws 120 and penetration jaws 130 in a closed configuration and compressing the tampon pledget 12. FIG. 17 is a schematic illustration of the compression apparatus 110 of FIG. 14 with the penetration jaws 130 in an open configuration and completely withdrawn from the tampon pledget 12 and the compression jaws 120 in a closed configuration.

Figure 18:
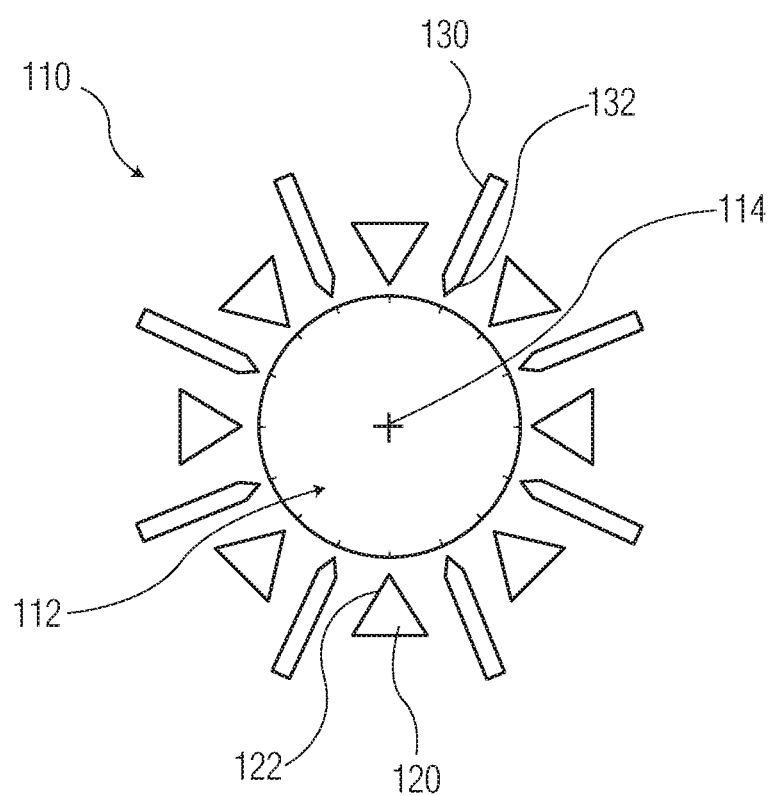
FIG. 18 is a schematic illustration of a compression apparatus wherein the compression jaws and penetration jaws move in a linear path towards the longitudinal axis of the compression space of the compression apparatus and wherein the compression jaws and the penetration jaws are in an open configuration.

In various embodiments, the compression jaws 120 and the penetration jaws 130 can be provided in a compression apparatus 110 wherein the compression apparatus 100 will open and close the compression jaws 120 and penetration jaws 130 in a radial direction along a linear path, such as compression apparatus 110 illustrated in FIG. 18. FIG. 18 is a schematic illustration of a compression apparatus 110 wherein the compression jaws 120 and penetration jaws 130 move in a linear path towards the longitudinal axis 114 of the compression space 112 of the compression apparatus 110 and wherein the compression jaws 120 and the penetration jaws 130 are in an open configuration.

Prior to the insertion of a tampon blank 30 into the compression space 112 of the compression apparatus 110, the compression jaws 120 and the penetration jaws 130 are in a fully open position, such as illustrated in FIG. 14 and FIG. 18, to allow for insertion of the tampon blank 30 into the compression space 112. The tampon blank 30 is inserted into the compression space 112 of the compression apparatus 110 and within the compression apparatus 110 the method 100 includes a step 104 of compressing the tampon blank 30 by utilizing the compression jaws 120 and the penetration jaws 130. The compression of the tampon blank 30 is accomplished by moving each of the compression jaws 120 and penetration jaws 130 in a direction towards a longitudinal axis 114 of the compression space 112 of the compression apparatus 110. As each of the compression jaws 120 and penetration jaws 130 are moved in a direction towards the longitudinal axis 114 of the compression space 112 the movement of each of the compression jaws 120 and penetration jaws 130 can be in either an arcuate path, such as illustrated in FIGS. 14-17, or a linear path, such as illustrated in FIG. 18.

The compression jaws 120 and the penetration jaws 130 are in an open position when the tampon blank 30 is inserted into the compression space 112 of the compression apparatus 110. The compression jaws 120, while in the open position, will make contact with the tampon blank 30 during the insertion of the tampon blank 30 to provide for concentric positioning of the tampon blank 30 into the compression space 112 of the compression apparatus 110. The penetration jaws 130, however, will not contact the tampon blank 30 during the insertion of the tampon blank 30 into the compression space 112 of the compression apparatus 110. The sidewalls 124 of the compression jaws 120 guide the tampon blank 30 such that the longitudinal axis of the tampon blank 30 is aligned with the longitudinal axis of the compression apparatus 110 during insertion of the tampon blank 30 into the compression apparatus 110 while the compression jaws 120 are in the open position. After the tampon blank 30 is inserted into the compression apparatus 110, the compression jaws 120 and the penetration jaws 130 move to a closed position during the compression step 104. In various embodiments, the compression jaws 120 operate independently from the penetration jaws 130. In various embodiments, the compression step 104 can occur via the sequential operation of the compression jaws 120 and the penetration jaws 130. In various embodiments, the compression step 104 can occur via a simultaneous operation of the compression jaws 120 and penetration jaws 130. In various embodiments, the compression jaws 120 and the penetration jaws 130 operate with a least a portion of the relative motion being asynchronous with each other. The concentric alignment of the tampon blank 30 by the compression jaws 120 during the insertion of the tampon blank 30 ensures that the tampon blank 30 is uniformly compressed from the initial diameter to form a compressed pledget 12 having a compressed diameter.

The method 100 also includes a step 106 of ejecting the pledget 12 from the compression apparatus 110 by retracting the penetration jaws 130 fully from the pledget 12 to the open configuration and maintaining the compression jaws 120 in a closed position such as illustrated in FIG. 17. Attempting to eject a pledget 12 from the compression apparatus 110 with the penetration jaws 130 either partially or fully in a closed position and with the penetration segments 132 at least partially engaged with the absorbent material 14 of the pledget 12 will result in damage to the pledget 12 as the absorbent material 14 of the pledget 12 can be snagged or scuffed by the penetration segments 132 located on the penetration jaws 130. The compression jaws 120 in the closed position maintains the pledget 12 in a concentric alignment with the longitudinal axis of the compression apparatus 110, maintains the pledget 12 in a fully compressed configuration, and maintains the pledget 12 within the longitudinal center of the compression space 112 of the compression apparatus 110 during the ejection of the compressed pledget 12 from the compression space 112. The compression jaws 120 thus concentrically guide the pledget 12 out of the compression space 112 of the compression apparatus 110 by remaining in the fully closed configuration. As described herein, having at least one sidewall 124 which is oblique to a radial plane directed outward from the longitudinal axis 114 of the compression space 112 can reduce any potential friction between the compressed pledget 12 and the compression segment 122 of the compression jaw 120. Following the ejection of the pledget 12 from the compression space 112 of the compression apparatus 110, the compression jaws 120 are retracted from the closed position to the open position. Throughout the operation of the method 100, the compression jaws 120 can dwell in a position that is either a full open position to receive a tampon blank 30 or a full closed position to eject a compressed tampon pledget 12. Neither the compression jaws 120 nor the penetration jaws 130 stop their movement at an intermediate position between the full open position or the full closed position to either receive a tampon blank 30 or eject a compressed tampon pledget 12 from the compression space 112 of the compression apparatus 110.

A pledget 12, and a result tampon 10, can be compressed according to the method 100 described herein. The pledget 12, and the resultant tampon 10, can have a linear channel 40 and a non-linear channel 50. The linear channel 40 is the result of the compression of the tampon blank 30 by the compression jaws 120. The non-linear channel 50 is the result of the compression of the tampon blank 30 by the penetration jaws 130. Penetration jaws 130 which are designed as described herein, a penetration jaw 130 with multiple discrete penetration segments 132, can produce a non-linear channel 50 that is a continuous channel extending in the longitudinal direction (Y) of the tampon 10. The non-linear channel 50 can have undulations in the radial depth direction (Z) and, in various embodiments, can also have undulations in the circumferential direction (X) of the tampon 10. As described herein, the undulations in the radial depth direction (Z) is a pattern of crests 80 and troughs 82. The troughs 82 are formed by the penetration into the tampon blank 30 by the penetration segments 132 of the penetration jaws 130. The crests 80 are formed as a result of the absorbent material 14 and cover material located between the segments of absorbent material 14 which is being compressed by the penetration segments 132 being pulled downward such as into a fold. The absorbent material 14 and the cover material can fold downwards even though not actually under compression due to a variety of properties. Such properties include the material properties of the cover material such as, percent stretch to failure, thickness, and tensile strength, as well as the density and moisture of the absorbent material 14. An additional property which influences the ability for the absorbent material 14 and cover material to fold include the distance between each penetration segment 132 whereas a distance greater than about 8 mm between the penetration segments 132 may not result in a crest 80 in the pledget 12. The shape and orientation of the penetration segments 132 has also been found to influence whether a fold downward of the absorbent material 14 occurs. For example, a square or rectangular shaped penetration segment 132 may not produce a crest 80 in the pledget 12, however, penetration segments 132 which have a variable width and wherein a taper in the variable width of one penetration segment 132 is nearby to a taper in the variable width of the next successive penetration segment has been found to result in a crest 80 in the pledget 12. Other factors which may influence the ability for the penetration jaw 130 to produce a crest 80 in a pledget 12 include the orientation of the penetration segments 132 to the longitudinal axis 114 of the compression space 112 of the compression apparatus 110, the extent of the distance of extension of the penetration segments 132 from the base surface 134 of the penetration jaw 130, and the amount of compression pressure utilized to form the non-linear channel 50 in the compression of the tampon blank 30 to a pledget 12.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. A tampon comprising:
   a) a compressed absorbent pledget further comprising:
      i) a longitudinal axis, an insertion end, a withdrawal end, an outer surface, and a longitudinal length measured from the insertion end to the withdrawal end;
      ii) a longitudinal direction, a circumferential direction, and a radial depth direction;
      iii) a linear channel extending in the longitudinal direction of the pledget;
      iv) a first non-linear channel which undulates in the radial depth direction of the pledget and has at least one crest and at least two troughs in the radial depth direction of the pledget wherein a distance between each trough is less than about 8 mm, and wherein the first non-linear channel has a first outer surface edge and a second outer surface edge opposed to the first outer surface edge and separated from the first outer surface edge a variable width in the circumferential direction of the pledget at the outer surface of the compressed absorbent pledget, and wherein the first non-linear channel undulates in the circumferential direction;
      v) a second non-linear channel which undulates in the circumferential direction wherein the undulations in the circumferential direction of the first non-linear channel are congruent with the undulations in the circumferential direction of the second non-linear channel; and
   b) a withdrawal string extending from the withdrawal end of the compressed absorbent pledget.

2. The tampon of claim 1 wherein the non-linear channel further comprises a first channel sidewall extending from the first outer surface edge and in a direction toward the longitudinal axis; a second channel sidewall extending from the second outer surface edge and in a direction toward the longitudinal axis wherein the first channel sidewall and the second channel sidewall join together at an inner surface; a first region wherein the inner surface is located at a first depth below the outer surface and a second region wherein the inner surface is located at a second depth below the outer surface wherein the second depth is closer to the longitudinal axis than the first depth.

3. The tampon of claim 2 wherein a distance between the first depth and the outer surface is from about 0.25 mm to about 0.75 mm.

4. The tampon of claim 2 wherein a distance between the second depth and the outer surface is from about 0.8 mm to about 1.35 mm.

5. A tampon comprising:
   a) a compressed absorbent pledget further comprising:
      i) a longitudinal axis; an insertion end, a withdrawal end, an outer surface, and a longitudinal length measured from the insertion end to the withdrawal end;
      ii) a longitudinal direction, a circumferential direction, and a radial depth direction;
      iii) a linear channel extending in the longitudinal direction of the pledget;
      iv) a first non-linear channel which undulates in the circumferential direction and undulates in the radial depth direction; and
      v) a second non-linear channel which undulates in the circumferential direction wherein the undulations in the circumferential direction of the first non-linear channel are congruent with the undulations in the circumferential direction of the second non-linear channel; and
   b) a withdrawal string extending from the withdrawal end of the compressed absorbent pledget.

6. The tampon of claim 5 wherein the non-linear channel further comprises a first outer surface edge and a second outer surface edge opposed to the first outer surface edge and separated from the first outer surface edge in the circumferential direction at the outer surface of the compressed absorbent pledget; a first channel sidewall extending from the first outer surface edge and in a direction toward the longitudinal axis; a second channel sidewall extending from the second outer surface edge and in a direction toward the longitudinal axis; a first region wherein the first outer surface edge is separated from the second outer surface edge by a uniform width in the circumferential direction at the outer surface of the pledget and wherein the first channel sidewall and the second channel sidewall join together at an inner surface located at a first depth below the outer surface; and a second region wherein the first outer surface edge is separated from the second outer surface edge by a variable width in the circumferential direction at the outer surface and wherein the first channel sidewall and the second channel sidewall join together at an inner surface located at a second depth below the outer surface of the pledget wherein the second depth is closer to the longitudinal axis than the first depth.

7. The tampon of claim 6 wherein a distance between the first depth and the outer surface is from about 0.25 mm to about 0.75 mm.

8. The tampon of claim 6 wherein a distance between the second depth and the outer surface is from about 0.8 mm to about 1.35 mm.

9. The tampon of claim 6 wherein the non-linear channel further comprises a plurality of first regions and a plurality of second regions wherein the first regions and the second regions are positioned in an alternating sequence in the longitudinal direction of the tampon.

10. The tampon of claim 5 further comprising a plurality of linear channels and a plurality of non-linear channels wherein the linear channels and the non-linear channels are positioned in an alternating sequence.

11. The tampon of claim 5 wherein the undulations in the depth direction of the non-linear channel have at least 2 radial depth direction troughs.

* * * * *